US012806019B2

(12) United States Patent
Havel et al.

(10) Patent No.: US 12,806,019 B2
(45) Date of Patent: Nov. 24, 2026

(54) DEVICES FOR PLACEMENT AND FIXATION OF ANNULOPLASTY BELT

(71) Applicant: Muffin Incorporated, West Lafayette, IN (US)

(72) Inventors: William J. Havel, West Lafayette, IN (US); Jeremy T. Newkirk, West Lafayette, IN (US); Rita Hadley, Otterbein, IN (US); Yun Zhou, Eden Prairie, MN (US)

(73) Assignee: Muffin Incorporated, West Lafayette, IN (US)

( * ) Notice: Subject to any disclaimer, the term of this patent is extended or adjusted under 35 U.S.C. 154(b) by 86 days.

(21) Appl. No.: 18/678,101

(22) Filed: May 30, 2024

(65) Prior Publication Data

US 2024/0315845 A1 Sep. 26, 2024

Related U.S. Application Data

(63) Continuation of application No. 17/097,623, filed on Nov. 13, 2020, now Pat. No. 12,029,648, which is a continuation of application No. PCT/US2019/032216, filed on May 14, 2019.

(60) Provisional application No. 62/671,645, filed on May 15, 2018.

(51) Int. Cl.
*A61B 17/04* (2006.01)
*A61F 2/24* (2006.01)

(52) U.S. Cl.
CPC ............ *A61F 2/2466* (2013.01); *A61B 17/04* (2013.01); *A61B 2017/0409* (2013.01); *A61B 17/0485* (2013.01); *A61B 2017/0488* (2013.01); *A61B 2017/0496* (2013.01); *A61F 2220/0075* (2013.01)

(58) Field of Classification Search
CPC ........ A61B 17/0485; A61B 2017/0409; A61B 2017/0488; A61B 2017/0496
See application file for complete search history.

(56) References Cited

U.S. PATENT DOCUMENTS

| | | | |
|---|---|---|---|
| 4,779,616 | A | 10/1988 | Johnson |
| 5,910,148 | A | 6/1999 | Reimels et al. |
| 6,716,224 | B2 | 4/2004 | Singhatat |
| 2005/0177180 | A1 | 8/2005 | Kaganov et al. |
| 2005/0250986 | A1 | 11/2005 | Rothe et al. |
| 2007/0244555 | A1 | 10/2007 | Rafiee et al. |

(Continued)

FOREIGN PATENT DOCUMENTS

| | | | | |
|---|---|---|---|---|
| CA | 2757497 | A1 * | 10/2010 | ....... A61B 17/12013 |
| WO | WO 2006034245 | A2 | 3/2006 | |
| WO | WO 2017193123 | A1 | 11/2017 | |

*Primary Examiner* — Jacqueline Woznicki

(74) *Attorney, Agent, or Firm* — Woodard Emhardt Henry Reeves & Wagner LLP

(57) ABSTRACT

Among other things, there are disclosed embodiments of devices used for minimally-invasive treatments, such as treatment of mitral valves. In a system for placing an annuloplasty belt around the heart, embodiments for tensioning a suture associated with the belt are provided, as are embodiments of a suture lock for holding the suture with the applied tension. A delivery device that permits placement and tensioning of such a belt and activation of the suture lock in one procedure is also disclosed. Methods for making and using these features are also disclosed.

10 Claims, 14 Drawing Sheets

(56) References Cited

U.S. PATENT DOCUMENTS

| | | | | |
|---|---|---|---|---|
| 2011/0313434 | A1* | 12/2011 | Kocaturk | F16G 11/14 606/148 |
| 2013/0158600 | A1* | 6/2013 | Conklin | A61B 17/0401 606/232 |
| 2013/0218175 | A1 | 8/2013 | Auerbach et al. | |
| 2013/0325115 | A1 | 12/2013 | Maisano et al. | |
| 2015/0094739 | A1 | 4/2015 | Norton et al. | |
| 2015/0342600 | A1 | 12/2015 | Kim et al. | |
| 2016/0324636 | A1 | 11/2016 | Rourke et al. | |
| 2017/0367693 | A1 | 12/2017 | Heneveld | |

* cited by examiner

DEVICES FOR PLACEMENT AND FIXATION OF ANNULOPLASTY BELT

REFERENCE TO RELATED APPLICATION

This application is a continuation of U.S. patent application Ser. No. 17/097,623 filed Nov. 13, 2020, which is a continuation of PCT/US2019/032216, filed May 14, 2019, which claims the benefit of U.S. Provisional Patent Application Ser. No. 62/671,645 filed May 15, 2018, each of which is hereby incorporated by reference in its entirety.

This invention was created in the performance of a Cooperative Research and Development Agreement with the National Institutes of Health, an Agency of the Department of Health and Human Services. The Government of the United States has certain rights in this invention.

FIELD OF THE DISCLOSURE

The present disclosure concerns devices and methods for delivering therapeutic devices within the body, for example around the heart. In particular, devices for placing, tensioning, and locking a therapeutic device (such as an annuloplasty belt) are disclosed.

BACKGROUND

Devices have been proposed for treatment of secondary tricuspid valve or mitral valve regurgitation. As an example, a compression belt has been previously disclosed (see U.S. Application Ser. No. 62/580,033, incorporated herein by reference in its entirety) that is delivered around the atrioventricular (AV) groove of the heart. Compression applied by the belt to the heart reduces the stretched tricuspid and/or mitral valve annulus size. In particular examples, a compression belt includes a flexible mesh that can shorten in length and, as it shortens, expands in its cross sectional diameter. Such expansion more broadly distributes the compressive forces along the AV groove and minimizes the risk of obstructing flow through the coronary arteries or veins. The compression belt is shortened through the use of one or more tensioning sutures or lines threaded through a central lumen of the belt. When the suture(s) are pulled, the two ends of the belt are brought toward each other. The belt shortens in length and expands in diameter as more tension is applied.

In particular embodiments, the suture(s) may pass through a locking device. The suture(s) may be pulled or otherwise moved through the locking device during tensioning of the belt. Once it has been determined that a satisfactory amount of tensioning has been applied, the locking device holds the suture(s) in their tensioned condition or position. The belt is thus maintained in its tensioned condition, supplying compression to the heart in the AV groove.

Such a locking device can be difficult to use in the context and location of the heart, particularly if the approach to the heart is performed minimally-invasively (e.g. by venous and/or arterial access to the right atrial appendage). The locking device must be small, appropriate for use in the body over a significant time period, suitable to hold the tensioning suture(s) as needed, and able to be remotely placed and actuated. Further, minimally-invasive devices for placement of the belt, for application of tension to and locking the suture(s), and for easy release of these items, may be needed. The following device embodiments meet the need for locking the suture(s) in place, manipulating the tensioning suture(s), anchoring, setting, and releasing the locking device, and releasing the tensioning suture(s) as may be necessary.

SUMMARY

Among other things, embodiments are shown of devices for minimally-invasive procedures that include providing tension on an implanted device. For example, an annuloplasty belt for the heart may require tension to be applied to it, as through an attached tensioning suture, and held in a therapeutic procedure. Embodiments of tensioning devices, suture locks, and delivery devices are disclosed herein.

Embodiments of a tensioning device for placing tension on a tensioning suture such as one connected to an annuloplasty belt, can include a tubular outer member having a lumen and a distal opening of the lumen, the tubular outer member having an end surface around the distal opening. A first wire, having an end portion around which the tensioning suture is passed, is within the lumen so that the end portion extends beyond the distal opening. A second wire has an end loop between two leg portions, and is within the lumen so that at least part of the leg portions are within the lumen and the end loop is outside of the tubular outer member beyond the distal opening. In an extended configuration, the end portion of the first wire extends beyond the end loop of the second wire. The tensioning suture passes one of (a) under and (b) through the end loop of the second wire, so that pulling the second wire engages the tensioning suture and pulls the tensioning suture. The first wire anchors the tensioning suture with respect to the second wire during the pulling. To keep the tensioning suture from being pulled into the lumen, the lumen may have a diameter the same as or slightly larger than the sum of the diameters of the portions of the first wire and second wire within the lumen.

In particular embodiments, the lumen of the outer member has an inner diameter, and wherein the end loop is larger (has a maximum lateral dimension that is larger) than the inner diameter of the lumen. The first wire may have a straight end portion that passes through the end loop of the second wire, and may include a bend in or adjacent an end portion to prevent premature withdrawal of the first wire. In the extended configuration in such cases, the tensioning suture passes around the end portion of the first wire between the end loop of the second wire and the end surface of the tubular outer member. The first wire can be retractable with respect to the second wire. In such a retracted configuration, the end portion of the first wire does not extend through the end loop of the second wire, but is below the end loop so that the tensioning suture can be passed out from between the end loop and the end surface of the tubular outer member. In other embodiments, the end portion of the first wire may have a looped end portion joining at least one leg, and in an extended configuration at least part of the end loop of the second wire is between the end surface of the tubular outer member and at least part of the looped end portion of the first wire. The tensioning suture passes through the end loop of the second wire and around the at least one leg of the first wire below the looped end portion of the first wire. In such cases, the first wire may be retractable with respect to the second wire. In that retracted configuration, the looped end portion of the first wire may be retracted relative to the second wire so that the tensioning suture does not pass around the at least one leg or the looped end portion of the first wire.

Embodiments of a suture lock for holding a tensioning suture in tension can include a housing having first and second laterally separated through holes extending between a distal surface and a proximal surface. The housing may also have a side hole through a side surface and adjacent the proximal surface, which communicates with the first through hole. A snare having an opening is within the first through hole and is adapted to move longitudinally through the first through hole. In embodiments with the side hole, an anchor wire may pass through a proximal portion of the first through hole and through the side hole. The suture lock has an open configuration in which the opening of the snare is at least partially out of the first through hole, and the tensioning suture passes through the opening of the suture and the second through hole of the housing. The suture can be freely translated with respect to the snare and the second through hole of the housing. In a locked configuration, the opening of the snare is within the first through hole and the tensioning suture is held against translation by the snare in a tortuous configuration.

In particular examples, the snare is a planar body and the opening is a middle eyelet allowing passage of the tensioning suture. The snare can include an upper eyelet for attachment to a portion of the tensioning suture and a lower eyelet for accommodating a trigger wire. The trigger wire can include a ball fixed to an end of the wire, the ball fitted into the lower eyelet of the snare, whereby pulling the trigger wire and ball pulls the snare through the first through hole of the housing. Embodiments of the snare can have at least one tab joined to and extending from a proximal portion of the snare. In the open configuration the at least one tab is bent toward the body of the snare by, and remains biased against, a wall of the first through hole of the housing. In the locked configuration the at least one tab is beyond the proximal surface of the housing and pivoted outward from the snare so that it prevents retraction of the snare into the first through hole. Among such examples, the snare could include two lateral tabs, both bent toward the body of the snare in the plane of the snare in the open configuration. Alternatively or additionally, at least one tab could extend out of the plane of the snare, so that in the open configuration the at least one tab is bent toward the plane of the snare and in the locked configuration the at least one tab pivots away from the plane of the snare. Other examples of a snare include a filament, and the opening is a loop in the filament. The housing may include an inset in the first through hole, so that in the locked configuration the tensioning suture engages the inset.

Embodiments of an integrated delivery system for an annuloplasty belt can include a delivery sheath, a pusher catheter within the delivery sheath and having an internal lumen, a suture lock (such as the embodiments noted above) connected to a distal end of the pusher catheter, an annuloplasty belt beside the pusher catheter within the delivery sheath and having a tensioning suture, and a tensioning device (such as the embodiments noted above) for applying tension to the tensioning suture, within the lumen of the pusher catheter and proximal of the suture lock. A first end or loop of the tensioning suture is fixed to a portion of the suture lock, a middle portion of the tensioning suture passes through the suture lock, and a second end or loop of the tensioning suture is connected to the tensioning device.

In particular embodiments, the lumen of the pusher catheter includes a proximal portion with a first inner diameter and an end chamber having a second inner diameter larger than the first inner diameter. The suture lock may be fitted within that end chamber of the pusher catheter. The suture lock can include a proximal side hole and the pusher catheter can include a side hole in a distal end, with the two side holds at least overlapping. A safety and/or anchor wire can extend through the side hole of the suture lock and the side hole of the pusher catheter to hold the suture lock and pusher catheter together. A trigger wire may be connected to the suture lock, by which the suture lock is moved to a locked configuration to lock the tensioning suture within the suture lock. The trigger wire and the safety and/or anchor wire can extend through the lumen of the pusher catheter.

Particular features of embodiments of a tensioner assembly can include any or all of the following. A tubular outer member or cannula is used to allow bidirectional control of the tensioning suture end, i.e. the suture can be both pushed and pulled. The ability to push the suture can be important as it allows relief of tension on the suture and around the annuloplasty belt without concern for frictional drag within the pusher and delivery sheath. The inner diameter of the tubular member or cannula is sized to prevent the tensioning suture from pulling to within the cannula. A retention wire retains the tensioning suture loop end, provided the release wire is in place. A release wire or loop locks or anchors the tensioning suture in place with respect to the retention wire, but easily releases the suture when withdrawn from the retention wire. A release wire using a loop shape prevents withdrawal of the release wire without a threshold amount of tension applied to the release wire to cause the loop to collapse back into the cannula. A rounded end of the release wire (whether a straight wire or a loop) makes it atraumatic or less likely to gouge the inside of other delivery system structures.

Particular features of embodiments of a suture lock assembly can include any or all of the following. A housing shape may fit or nest into the end of the pusher catheter. Locking the suture uses a snare approach, pulling the suture into a pinch point and creating a tortuous (e.g. S-shape) arrangement in the suture to lock it. The housing may have a conical surface or chamfer on the entry point for the snare and the suture, allowing the lock to engage with minimal pull force on the snare or push force on the housing. The housing may have a through hole (separate from the hole for the snare) for the tensioning suture to pass smoothly through the lock and into the lumen of the pusher below. Embodiments of the snare can have an eyelet at the top of the snare for fixedly attaching one of the ends of the belt (e.g. via a part of the tensioning suture), and a middle eyelet for passage of the tensioning suture. These eyelets can be polished to provide smooth edges to prevent cutting the suture passing through them. A bottom eyelet n the snare can confines a ball mounted to the end of the trigger wire, the ball able to release from the lock when the snare is pulled sufficiently far into the housing. The snare may have a width enlargement at its top to prevent the snare from sliding all the way through the housing. A set of one or more latching tabs can be provided on the snare that emerge from the bottom of the housing and widen as the snare is pulled down. The position of such latching tab(s) are such that they emerge from the bottom of the housing before the trigger ball can escape from the snare. A side hole in the housing can provide an attachment point for a wire that serves to anchor the lock to the pusher catheter and prevents premature passage of the snare downward through the housing and locking of the lock.

Methods for delivery can include one or more of the following steps, in a sequence as indicated or in another sequence as the user may prefer. The annuloplasty belt is initially loaded onto a delivery frame which starts out loaded in the delivery sheath at a location distal to the suture lock and pusher catheter. The delivery sheath is pulled back to expose the frame, or the frame is extended from the delivery sheath, causing the frame and belt to expand and encircle the heart. The belt, still loaded on the frame, is tensioned, by sliding the tensioner down within the pusher catheter while the tensioning suture is held by or locked to the tensioner. Once the excess belt slack is taken up, the delivery frame is withdrawn alongside the pusher catheter. The tension on the belt is adjusted by further positioning of the tensioner (pulling or pushing the tensioning suture), e.g. by sliding the tensioner within the pusher catheter toward or away from the suture lock and annuloplasty belt. With proper tension established, the safety/anchor wire is pulled, which unblocks the lock trigger wire or otherwise allows its use, enabling the lock to be locked. Pulling the safety/anchor wire also allows release of the suture lock from the pusher catheter. The lock trigger wire is then pulled, causing the snare to move further into the housing and pulling the tensioning suture to a locked position. Pulling the trigger wire latches the snare in place and allows the ball at the end of the trigger wire to escape. Alternatively, the lock trigger wire can be kept held in position and the pusher catheter advanced to push the lock housing forward while the snare stays in place, resulting in the same locking, latching and trigger wire release. The release wire or loop is pulled from the tensioner, causing the tensioning suture to release from the tensioner. The delivery sheath is withdrawn, leaving the belt, tensioning suture and lock within the body.

DESCRIPTION OF THE ILLUSTRATED EMBODIMENTS

Figure 1:
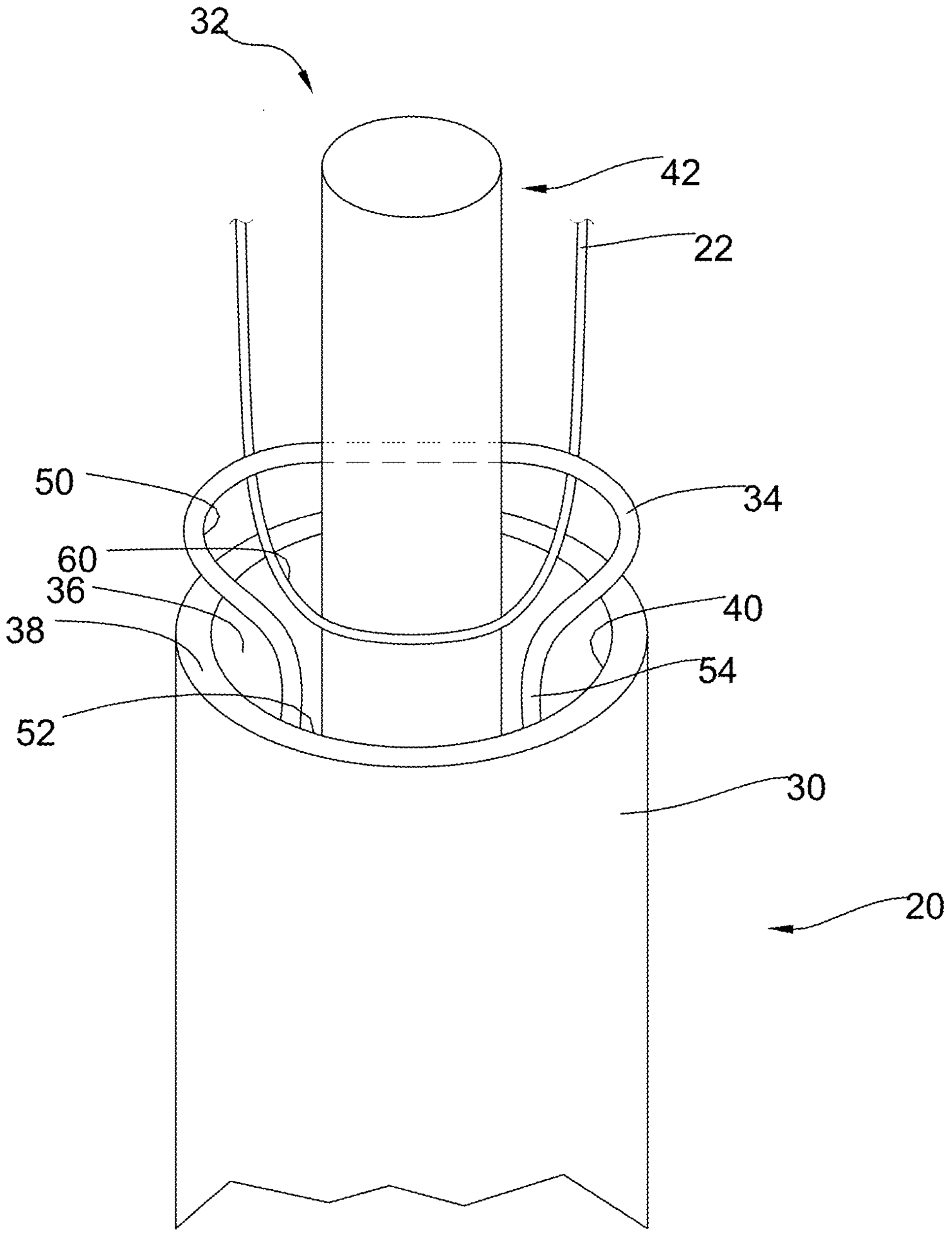
FIG. 1 is a perspective view of an embodiment of a tensioning device according to the disclosure.

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the disclosure is thereby intended. Any alterations and further modifications in the described embodiments and any further applications of the principles of the present disclosure as described herein are contemplated as would normally occur to one skilled in the art to which the disclosure relates.

Turning now to the drawings, there is shown in FIG. 1 an embodiment of a tensioning device 20 for applying tension to a suture 22. Suture 22 is threaded through or otherwise attached to a compression belt (FIG. 14) which is or is intended for placement in or adjacent to the AV groove of the heart. In particular embodiments, when the belt is so placed, pulling or otherwise applying tension to suture 22 results in (1) a compressive force on the belt to compress the heart, and (2) a shortening of the length of the belt and concomitant widening of the tubular belt, to protect veins, arteries or other cardiac structures.

Device 20 is able to be placed minimally-invasively, e.g. through a sheath or catheter as described below, and is connected to suture 22. In particular embodiments, device 20 engages suture 22 directly, and may be so engaged prior to the placement of the compression belt around the heart. Device 20 includes a tube or cannula 30, a first release and anchoring wire 32 and a second holding wire 34. Tube 30 acts as a holder and passage for wires 32, 34, having a lumen 36 through which wires 32, 34 extend. In particular embodiments, tube 30 is of a flexible material, able to traverse a path through the vasculature without kinking. Exemplary materials include nitinol or stainless steel. The inner diameter of tube 30 may be small, e.g. just large enough to accommodate wires 32, 34, so as to prevent or limit tensioning suture 22 from pulling into the end of tube 30. Tip 38 of tube 30 may have rounded leading edges to minimize risk of tip 38 gouging the interior of a piece through which tensioning device 20 is moved, such as a pusher catheter (discussed below). Wires 32, 34 may be biocompatible, e.g. nitinol or stainless steel.

Wire 32 in the embodiment of FIG. 1 is a straight member, with an end portion 42 that extends to and through opening 40 of tube 30. As used herein, "wire" indicates an elongated thin member having a rigidity sufficient to apply tension to suture 22 as described herein. It may be of metal, or of other substances having such characteristics. Wire 32 may have a constant diameter overall, or in portion 42. In the illustrated embodiment, the maximum width of portion 42 (or of the entire wire 32) is substantially less than the width of lumen 36 of tube 30, for example half the width of lumen 36 or less. In the illustrated embodiment, wire 32 is centrally-located within lumen 36, or at opening 40 of lumen 36, and acts as a center anchor or support for suture 22.

In the illustrated embodiment, wire 32 is straight throughout, including end portion 42. Alternatively, wire 32 can include a bend in end portion 42 or setting off a straight end portion 42. For example, a bend may be heat-set in a portion of wire 32 as a border to end portion 42, and the bend may be positioned beyond tip 38, i.e. exposed from lumen 36. The bend may position at least a portion of end 42 over tip 38 of tube 30 in an initial configuration or when tensioning device 20 is in a mode suitable for tensioning suture 22, as described herein. In that way, the bend and/or end portion 42 helps prevent premature or unintended withdrawal of wire 32, as discussed further below. In particular examples, the bend may form a planar angle in wire 32, such as an obtuse, right or acute angle, although an obtuse angle (e.g. greater than 135 degrees) may be preferred so that wire 32 (or end portion 42) does not damage or interfere with the inside of tube 30, other parts of tensioning device 20, and/or a delivery sheath or other components within it (as discussed further below). In other embodiments, a more complicated bend (or more than one bend) may be placed in wire 32, such as a part-helical (pig-tail) or other curved shape.

Wire 34 is a looped member in the embodiment of FIG. 1. In a particular embodiment, wire 34 has a loop 50 between two leg portions 52, 54. Loop 50 is shown as open in the illustrated embodiment, having a gap 56 between leg portions 52, 54. In other embodiments, loop 50 may be closed, with leg portions 52, 54 joining each other (e.g. welded or glued together) or wrapped or twisted together. Loop 50 extends out of tube 30, i.e., beyond opening 40, in this embodiment, and may have a maximum outer width measured between the outer surfaces of opposed parts of loop 50 that is larger than the inner diameter of opening 40 or larger than the outer diameter of tube 30 at or near end surface 38. In such embodiments, the size of loop 50 prevents loop 50 from being drawn into tube 30 through opening 40. As seen, loop 50 may be in a plane that is oblique or perpendicular to the central axis of wire 32 and/or lumen 36. One or both of leg portions 52, 54 extend into lumen 36. Such leg portion(s) 52 and/or 54 may extend through the entirety of tube 30, or may be operatively connected to a control device (not shown).

In this embodiment of device 20, first or straight wire 32 extends centrally (or approximately so) within lumen 36 of tube 30. Wire 32 also extends through loop 50 of wire 34. That is, loop 50 passes around at least part of wire 32, and one or both leg portions 52, 54 extend into lumen alongside at least part of wire 34. Tensioning suture 22, both ends of which are connected to the compression belt, has a loop or bight 60 that engages device 20. In the illustrated embodiment, suture 22 runs under loop 50 of wire 34 (i.e. between loop 50 and end 38 of tube 30), around wire 32, and out again under loop 50. As seen in FIG. 1, loop 50 of wire 34 passes generally around one side of wire 32, and loop 60 of suture 22 passes generally around the other side of wire 32. Suture 22 thus cannot be removed from device 20 unless (1) wire 32 is removed, or (2) suture 22 is cut or detached from the compression belt.

Figure 14:
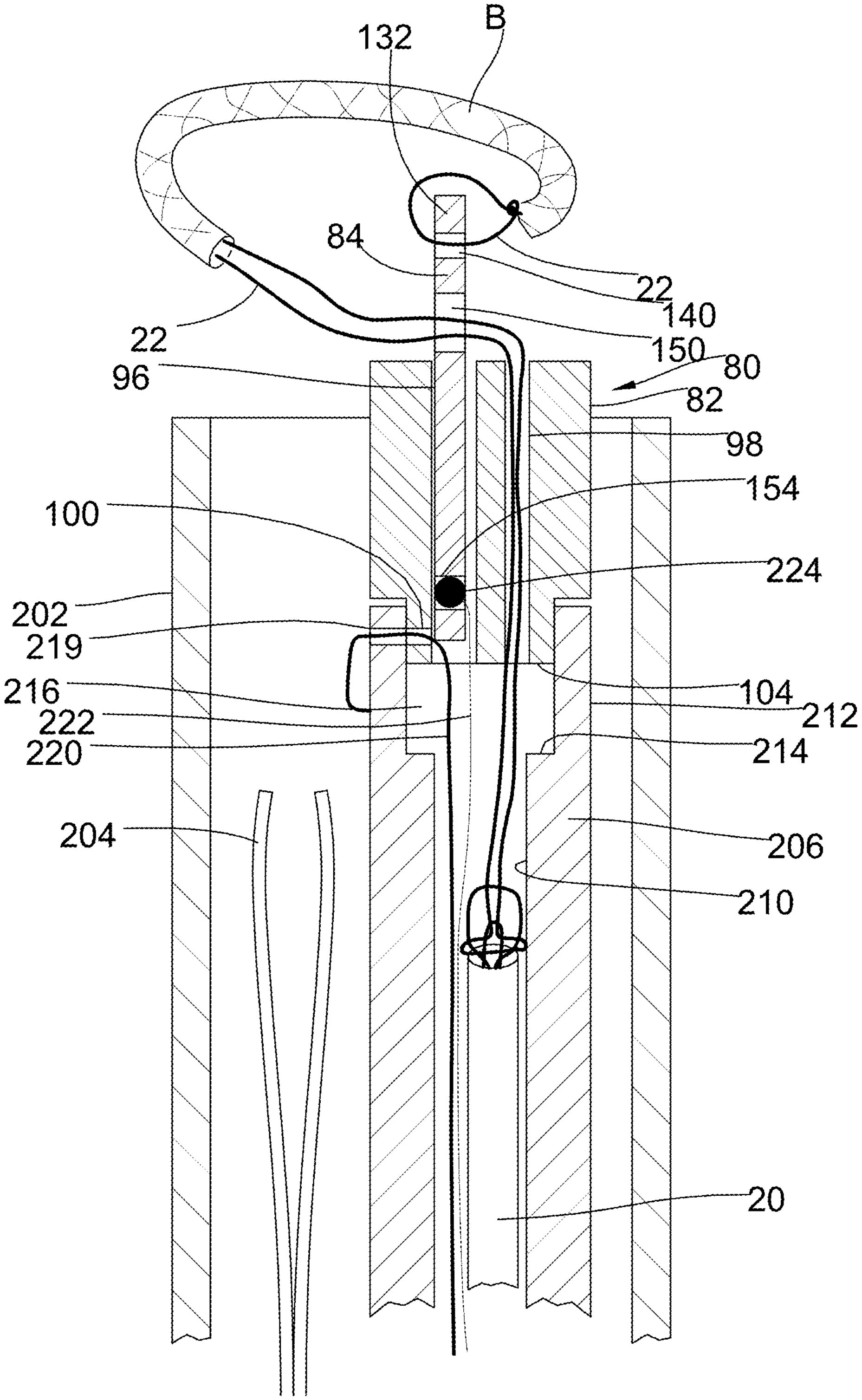
FIG. 14 is a part cross-sectional view of an embodiment of an integrated delivery system for a medical device, shown as an annuloplasty belt in that embodiment, and including structures shown in prior figures.

In operation, as noted above loop 60 of the tensioning suture 22 passes under loop 50 of wire 34 and around the wire 32, and is effectively locked to device 20. A handle (not shown) is connected to tube 30 and wire 32, and in some embodiments to wire 34, so as to allow the user to advance and retract tube 30, wire 32 and/or wire 34. To adjust tension, the user operates the handle to controls the position of tube 30, wire 32 and wire 34, either individually or in combination. For example, retracting at least wire 34, preferably as a unit with tube 30 and perhaps wire 32, pulls suture 22 along with wire 34. Loop 50 of wire 34 engages loop 60 of suture 22, and because suture 22 is fixed to the compression belt and is looped around wire 32, suture 22 is pulled along with wire 34. The rigid nature of tube 30 allows bi-directional control of the position of suture 22, i.e. tube 30 (and/or wires 32, 34) can both pull and push loop 60 and suture 22 within a delivery sheath (FIG. 14). That is, advancing tube 30 allows end 38 to engage suture 22 and move it forward, either alone or in conjunction with loop 50 of wire 34. For example, advancing tube 30 may allow loop 60 of suture 22 to be gripped between surface 38 of tube 30 and loop 50 of wire 34, and as tube 30 and wire 34 move forward, suture 22 moves forward as well. If suture 22 is already under tension, such tension can be reduced by advancing tube 30 and/or wire 34.

Once the appropriate amount of tension has been applied to suture 22, as by retraction of wire 34 and/or tube 30, tension can be locked using a suture lock as described below, or by another suitable locking mechanism. When locked, suture 22 is released from device 20 by withdrawing wire 32 into or through lumen 36 of tube 30. In embodiments in which wire 32 includes a bend, as discussed above, the bend adds resistance to the withdrawal, providing some protection from premature or unintended release. For example, engagement between end portion 42 and tip 38 and/or wire 34 caused by the bend can provide slight resistance that pulling of wire 32 must overcome. Pulling wire 32 straightens it at or adjacent the bend (e.g. reducing or eliminating the bend), and allows wire 32 to move through or into lumen 36 of tube 30. In embodiments in which wire 32 is operatively connected to a handle (not shown), the operator operates the handle to retract wire 32, while maintaining the position of wire 34 and tube 30. Once the forward end of wire 32 is past loop 60 of suture 22 (and/or past loop 50 of wire 34), suture 22 is free to pass from between loop 50 and tube 30, and is released from device 20.

It will be understood that device 20 may be or be part of a stand-alone device, or may be a component of another device. For example, the structures and features discussed above with respect to device 20 may be packed within a delivery device for a compression belt, such as the embodiment of an integrated placement device discussed below, with device 20 behind the compression belt and a locking mechanism for holding suture 22. Once the compression belt and associated locking mechanism is delivered from that delivery device, operation of device 20 to tension suture 22 can occur.

To summarize, use of tensioning device 20 with its tube 30 allows bidirectional control of an end of tensioning suture 22, i.e., the suture can be both pushed and pulled. The ability to push suture 22 can be important as it allows relief of tension around the annuloplasty belt without concern for frictional drag within a delivery device (e.g. pusher catheter and/or delivery sheath discussed below). A retention trigger loop 50 retains loop 60 of tensioning suture 22 provided the release trigger wire 32 is in place. The release trigger wire 32 or trigger loop that locks tensioning suture 22 in place easily releases suture 22 when wire 32 is pulled back or withdrawn. The end of release trigger wire 32 is rounded to make it atraumatic or less likely to gouge the inside of other delivery system structures (discussed below). The release trigger can use a loop shape to prevent withdrawal without a threshold amount of applied tension to cause the loop to collapse back into tube 30.

Figure 2:
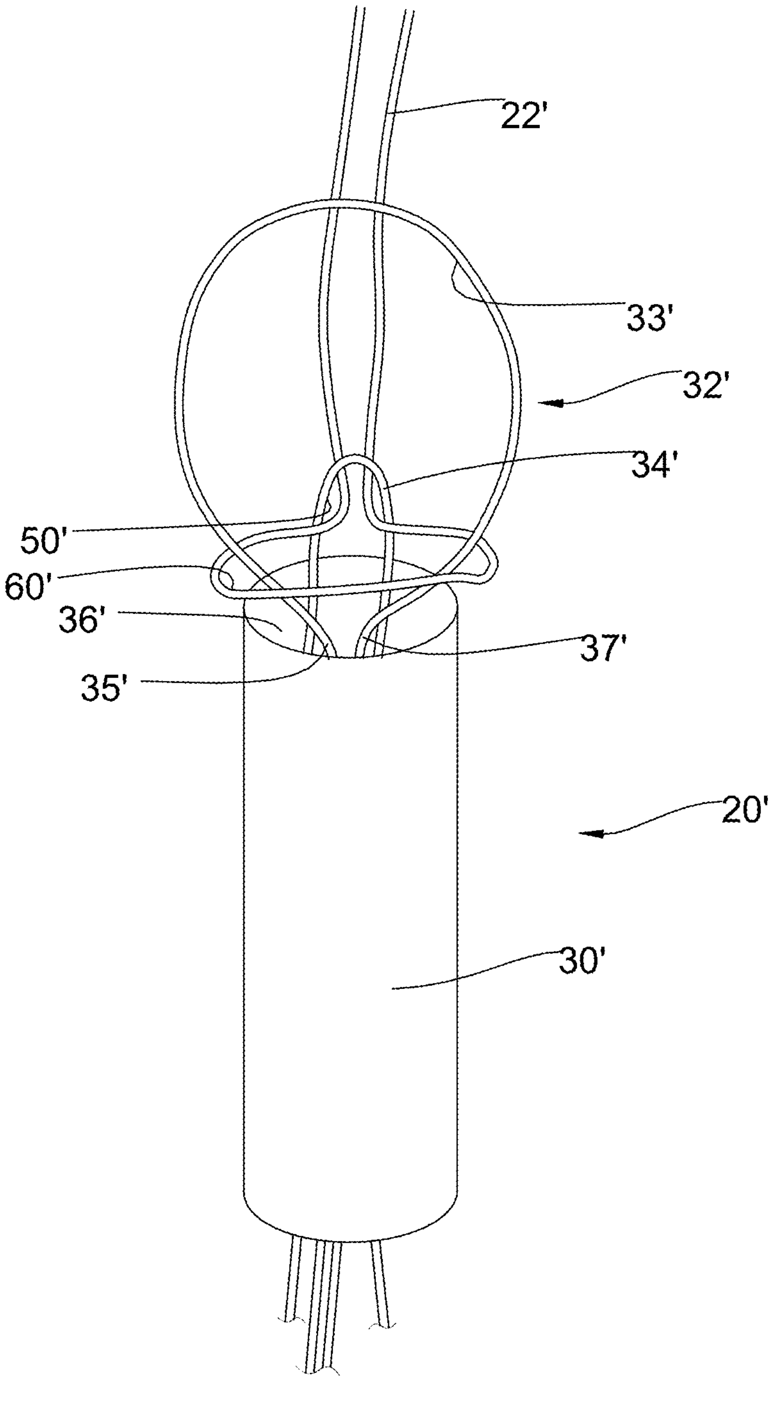
FIG. 2 is a perspective view of an embodiment of a tensioning device according to the disclosure.
Figure 3:
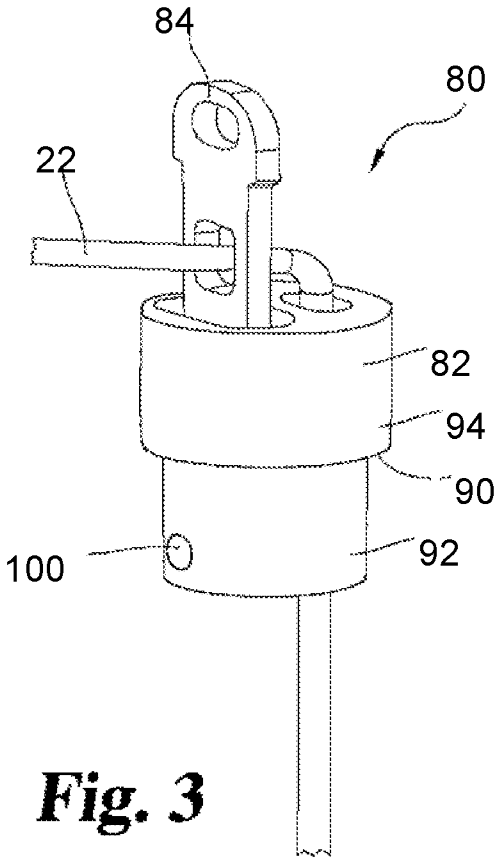
FIG. 3 is a perspective view of an embodiment of a suture lock device with a tensioning suture in an open or unlocked condition, according to the disclosure.
Figure 4:
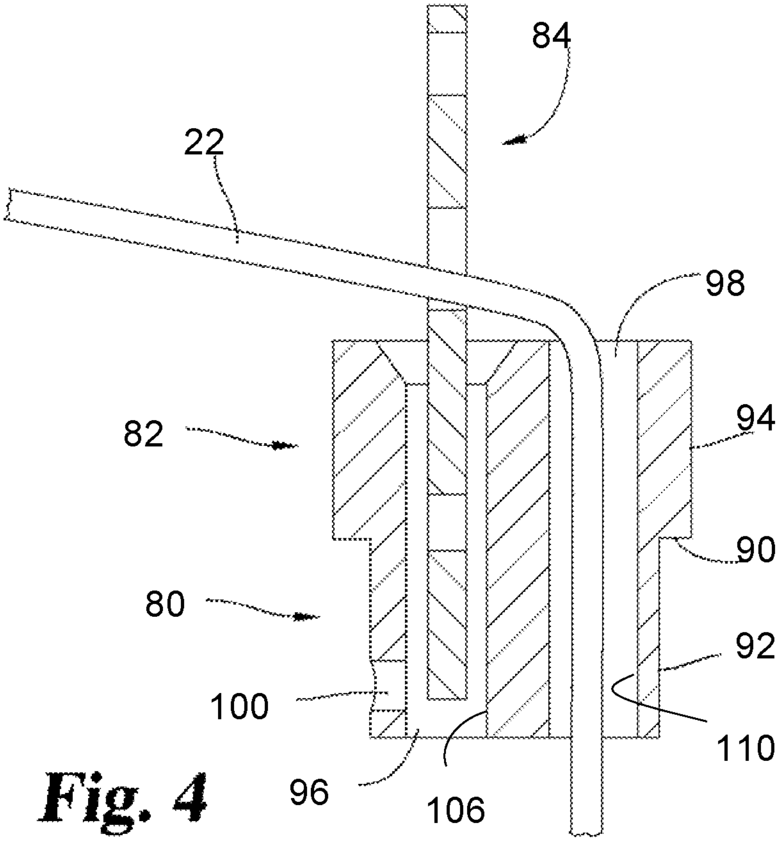
FIG. 4 is a perspective view of the embodiment FIG. 3 in a locked condition.

In a related embodiment, a tensioning device 20' is shown. In most respects, device 20' is the same as device 20. The principal difference is that wire 32 of device 20 is replaced with a looped wire 32', so that device 20' has two looped wires 32' and 34'. Tube 30' is the same in this embodiment as tube 30, having a central lumen 36'. Wire 34' includes loop 50', which in this embodiment may be in a plane parallel to the central axis of lumen 36'. In this embodiment of device 20', wire 32' (with loop 33' and leg portions 35' and 37') extends centrally (or approximately so) within lumen 36' of tube 30'. Wire 32' (or specifically one or both leg portions 35', 37') may include one or more bends as described above with respect to wire 32, and in particular embodiments the bend(s) may turn or curve loop 33' away from wire 34'. Wire 34' also extends into or through lumen 36' alongside wire 32', so that loop 50' and loop 33' are next to and generally parallel to each other. Tensioning suture 22', which is connected to the compression belt, has a loop 60' that engages device 20'. In the illustrated embodiment, suture 22' runs through loop 50' of wire 34', around a lower portion of loop 33' (and/or legs 35', 37') of wire 32', and back through loop 50'. As seen in the example of FIG. 2, loop 60' of suture 22' is smaller in diameter than the diameter or largest width of loop 33' of wire 32'. Suture 22' thus cannot be removed from device 20' unless (1) wire 32' is removed, or (2) suture 22' is cut or detached from the compression belt.

The operation of the embodiment of device 20' is essentially identical to the illustrated embodiment of device 20. At least wire 32', and in particular examples the combination of tube 30' and wires 32' and 34', are retracted or advanced (e.g. by a handle, not shown) to control the position of loop 60' of tensioning suture 22'. As discussed above, retracting device 20' (or appropriate parts of it) pulls suture 22' to place it in tension, and advancing device 20' reduces tension and/or repositions suture 22'. When the operator is ready to release suture 22', e.g. when the proper tension is applied and locked into suture 22', wire 32' is pulled through loop 60' of suture 22', leaving suture 22' to easily slide out through loop 50' of wire 34'.

Wire 32' is preferably heat set or otherwise configured so that its loop 33' has a wider radius of curvature than that of loop 50' of retention wire 34'. As such, wire 34' is more difficult to inadvertently pull through suture 22' or into lumen 36' when assembling device 20' itself, or incorporating it into another device (e.g. a delivery system for a compression belt as discussed above). Another advantage in using a looped wire 32' in place of a straight wire 32 is that loop 33', as the forward end or tip of wire 32', is more atraumatic than is the tip of straight wire 32.

Lock Concepts

Turning now to FIGS. 3-13, there is shown an embodiment of a suture lock 80, that allows a suture 22 (e.g. one connected to a compression belt (FIG. 14) as discussed herein) to freely slide through it in an unlocked state, but permanently restricts motion of suture 22 when locked. In the illustrated embodiment, lock 80 includes two components, a housing piece 82 and a snare piece 84. Snare 84 fits into and is movable within housing 82, as will be discussed further below. Suture 22 passes through snare 84 and housing 82, and is movable with respect to both when lock 80 is unlocked. Lock 80 is locked by moving snare 84 with respect to housing 82 so as to grip or pinch suture 22.

The illustrated embodiment of housing 82 is rigid and generally in the shape of a cylinder, with an external step 90 changing the diameter of housing 82 from a narrow region 92 to a wider region 94. Narrow region 92 allows housing 82 to be engaged or fit into a pusher catheter (FIG. 14). That fit may be a close fit that stabilizes the position of lock 82 during delivery, and provides counter traction when suture 22 is pulled through lock 80 during tensioning of suture 22. Lock 80 also includes a first through hole 96 that accommodates snare 84, and a second through hole 98 that provides a passage through housing 82 for a portion of suture 22. A small side hole 100 is provided in housing 82 that serves as an anchor point for a safety wire that both anchors lock 80 and a compression belt to a pusher catheter and thereby prevents premature activation of lock 80.

Through hole 96 extends from an upper or distal surface 102 to a lower or proximal surface 104 of housing 82. Hole 96 is straight (i.e. linear) in the illustrated embodiment and is bounded by a wall 106. As a particular example, hole 96 may have a central longitudinal axis that is perpendicular to both upper surface 102 (an end in wider region 94) and lower surface 104 (an end in narrow region 92), and parallel to the cylindrical side surfaces of narrow region 92 and wider region 94. Hole 96 is oblong in this embodiment, having a first lateral dimension that is less than a second lateral dimension, these lateral dimensions being perpendicular to each other. In a particular example, hole 96 is generally in the shape of a rounded rectangle, with opposing side planar surfaces and corner quarter-cylindrical surfaces.

Wall 106 has a lower or proximal portion **106*a* in the illustrated embodiment in which the first and second lateral dimensions are constant. Adjacent upper surface 102, hole 96 widens in both lateral dimensions in the illustrated embodiment, and in a particular example has a conical wall portion or chamfer 106*b* widening from wall portion 106*a* within housing 82 to a larger diameter at upper surface 102. The widened portion 106*b* limits or eliminates sharp corners, particularly 90-degree corners that may damage or provide a stress point on a suture 22, and provides an easy entrance for suture 22 as further noted below. The lateral dimensions are sized to accommodate snare 84**, as will be further described below, and in a particular embodiment the larger lateral dimension may be twice the size of the smaller lateral dimension.

Through hole 98 is an oblong hole in the illustrated embodiment, having a wall 110 with two flat or planar middle sections **110*a* and two end semi-cylindrical sections 110*b*. A smaller lateral dimension is measured between the planar sections 110*a*, and a larger lateral dimension is measured between the centers of sections 110*b*. In a particular embodiment, the larger lateral dimension of hole 98 is the same or approximately the same as the larger lateral dimension of wall section 106*a* of hole 96. The smaller lateral dimension of hole 98 may also be the same or approximately the same as the smaller lateral dimension of hole 96. Hole 98 extends from upper surface 102 to lower surface 104. Hole 98 and its wall 110 is separated from hole 96 and its wall 106 so that no part of holes 96, 98 overlap or intersect. Hole 98 has a central longitudinal axis that is parallel to the central longitudinal axis of hole 96, and perpendicular to surfaces 102, 104, in this embodiment. Hole 96 may have corners at surfaces 102, 104**, or may be beveled or otherwise treated to minimize corners.

Hole 100 is in narrow region 92 of housing 82, adjacent to but not intersecting lower surface 104. Hole 100 has a cylindrical wall 112 in the illustrated embodiment, and extends from the outer surface of housing 82 to hole 96. In the illustrated embodiment, hole 100 has a central longitudinal axis that is perpendicular to the central longitudinal axis of hole 96, and parallel to surfaces 102, 104. The inner diameter of hole 100 may be small, for example just large enough to pass a trigger wire or other control mechanism.

Snare 84 has a thin planar body 120 in the illustrated embodiment, having first and second ends 122, 124 and a middle portion 126. Opposing planar surfaces 128, 130 extend through ends 122, 124 and portion 126. End 122 has a dome-shaped head 132 with rounded end corners 134, and which is wider than middle portion 126. In the illustrated embodiment, head portion 132 meets middle portion 126 at a sharp step or boss 136 on both sides, with a surface 138 that is perpendicular to middle portion 126 and generally faces toward end 124. Head portion 132 includes an upper eyelet 140 that is oblong or oval, and in a particular embodiment has upper and lower planar surfaces 142*a*, 142*b* between circular or cylindrical surfaces 144*a*, 144*b*. Eyelet 140 extends all the way through head portion 132, from surface 128 to surface 130 with openings in each surface.

Middle portion 126 has two straight sides 146 extending from respective bosses 136 toward end 124. A sharp step or boss 148 is inset from each side 146. A middle eyelet 150 extends through middle portion 126, with openings in each surface 128, 130. In the illustrated embodiment, eyelet 150 is in the shape of a rectangle (e.g. a square) with rounded corners. Eyelet 150 is positioned closer to bosses 136 than to bosses 148 in a particular embodiment, and in one example the edge of eyelet 150 closest to end 124 is from one-third to two-fifths of the way from bosses 136 to bosses 148. A lower eyelet 154 is at least partially in middle portion 126. In the illustrated embodiment, eyelet 154 is circular and extends all the way through body 120, with openings in surfaces 128, 130. Eyelet 154 may intersect the plane of bosses 148 (see, e.g., FIG. 11).

Figure 11:
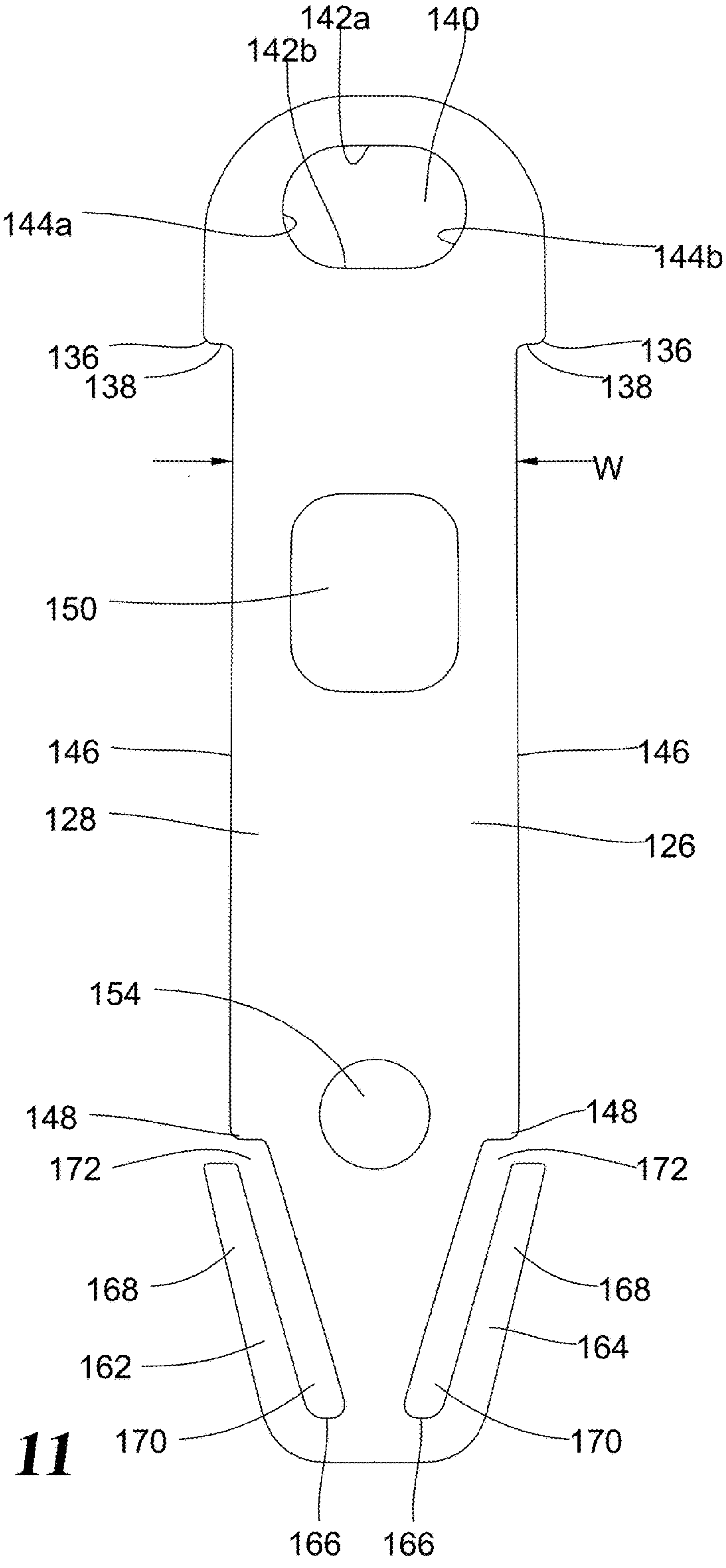
FIG. 11 is a side elevational view of the embodiment of FIG. 10.
Figure 12:
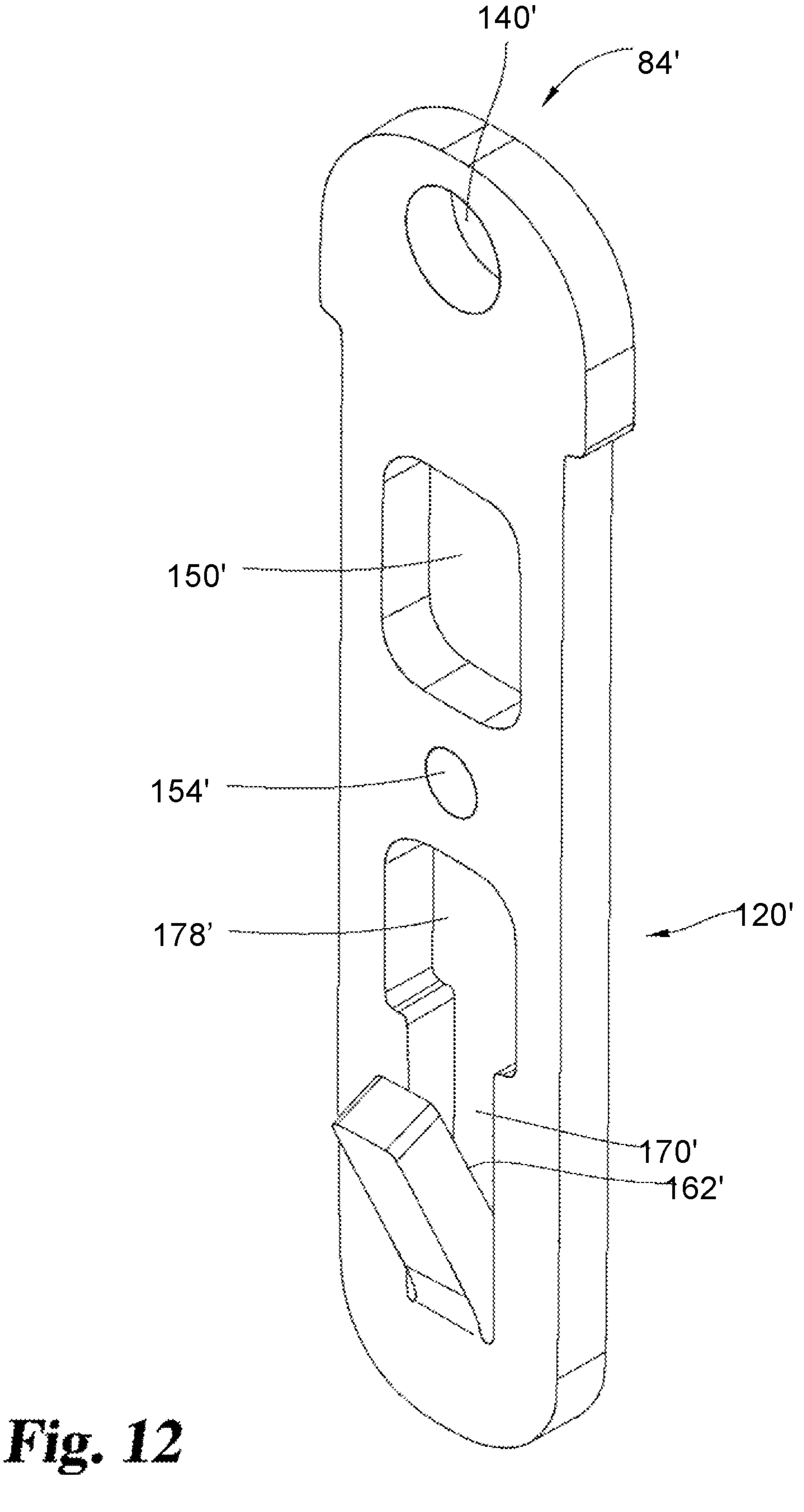
FIG. 12 is a perspective view of an embodiment of a snare usable with embodiments of a housing such as that of FIG. 8.

End 124 includes a tail portion 160 that includes tabs 162, 164. Tabs 162, 164 are generally L-shaped, each having a respective tip 166 that extends from body 120 and a respective leg 168 that extends from tip 166. In the illustrated embodiment, each leg 168 is linear and extends from tip 166 away from (e.g. obliquely with respect to) a central longitudinal axis of body 120 and toward end 122. As seen in the drawings (e.g. FIGS. 10-11), each leg 168 defines a respective channel 170 between itself and body 120. For example, such channels 170 may be parallel to their respective leg 168, with an outlet 172 between leg 168 and the adjacent boss 148. In such an embodiment, the portion of body 120 adjacent legs 168 and bosses 148 is essentially V-shaped. Eyelet 154 may be at least partially within that V-shaped portion of body 120, and one or both tips 166 may engage body 102 at the apex of that V-shaped portion, as best seen in FIG. 11. Tabs 162, 164 may pivot toward and away from the central longitudinal axis of body 120, e.g. around respective tips 166 or the points where respective legs 168 meet their tips 166, as will be discussed further below.

Body 120 is a linear plate in which eyelets 140, 150, and 154 are cut and polished to smooth their respective edges and limit the potential for damage to suture 22, in the illustrated embodiment. In particular embodiments, tabs 162, 164 are formed by cuts into body 120 that create channels 170. In other embodiments, body 120 may be formed by molding or other processes. As with housing 82, snare 84 may be of a rigid biocompatible material, such as stainless steel, titanium, sturdy polymers, or similar substances or compounds.

Snare 84 fits within hole 96 of housing 82, and is movable from an open position, in which eyelet 140 and at least part of eyelet 150 are exposed over surface 102 of housing 82, and a locked position in which tabs 162, 164 extend from and lock with respect to surface 104 of housing 82. The respective widths of the parts of snare 84 are chosen so as to allow such movement and locking of suture lock 80. In one example, the width W of middle portion 126 of body 120 is less than or equal to the inner diameter (or larger dimension between opposing portions of wall 106*b*) of hole 96 of housing 82. Tabs 162, 164 have a maximum width (e.g. adjacent respective bosses 148) in an unstressed or unfolded condition that is larger than the inner diameter (or larger dimension between opposing portions of wall 106*b*) of hole 96 of housing 82. Head portion 132 of body 120 is larger in width than portion 106*b* of hole 96, but may be equal to or smaller than a dimension of chamfer or conical section 106*a* of hole 96.

In particular embodiments, bottom eyelet 154 of snare 84 confines or holds a ball mounted to the end of a trigger wire (see, e.g., 222, 224 in FIG. 14). A portion of the wire may pass along through hole 96 of housing 82 with snare 84. As the wire is pulled, the ball fixed to its end forces snare 84 down further into hole 96. When snare 84 has been pulled sufficiently through housing 82, the ball clears bottom surface 104 of housing 82. In particular examples, the ball clears bottom surface 104 at the same time or just after tabs 162, 164 clear surface 104 and expand to lock snare 84 with respect to housing 82. The wire and ball may thus be removed from suture lock 80 and withdrawn through a placement device. A separate wire (e.g. 220 in FIG. 14) through side hole 100 holds or assist in holding lock 80 to a delivery device, and/or to prevent premature passage of snare 84 downward through housing 82.

Thus, snare 84 has a top eyelet 140 for anchoring to the belt, a second, mid-eyelet 150 that allows free passage of tensioning suture 22 in the unlocked state but which restricts motion of tensioning suture 22 in the locked state, and a bottom eyelet 154 used with a trigger wire for lock activation. The width of snare 84 near its top is slightly increased to prevent snare 84 from being pulled completely through housing 82. At the bottom of snare 84, there is a pair of tabs 162, 164 that extend wider than snare body 126 and pop out, latching snare 84 in place when it is pulled to its lowermost or proximal-most position and tabs 162, 164 extend below bottom surface 104 of housing 82. The top and mid eyelets 140, 150 are preferably electropolished or mechanically polished to round the edges and allow smooth passage of suture through without cutting or tearing the suture.

Tensioning Suture Pathway and Lock Activation

In use, a tensioning suture 22 travels from an annuloplasty belt to which it is attached through middle eyelet 150 of snare 84 and into through hole 98 of housing 82. The belt is attached to eyelet 140 in head portion 132 of snare 84, for example by an opposite end of suture 22. Suture 22 extends through all of hole 98 and to or toward a tensioning device (such as an embodiment of device 20 described above). In the unlocked state (e.g. FIGS. 3-4), snare 84 is positioned with respect to housing 82 so that middle eyelet 150 is clear (e.g. fully above) surface 102 of housing 82. Suture 22 is freely and smoothly translatable through eyelet 150 and through hole 98, so that suture 22 can be placed in tension as described above. Tabs 162, 164 are within through hole 96 and forced inward with respect to V-shaped portion of body 120 by the inner wall 106 of through hole 96. In that condition, one or both channels 170 are partially or completely closed or narrowed from the unstressed condition, and tabs 162, 164 are biased against the inner wall 106 of hole 96.

Figure 5:
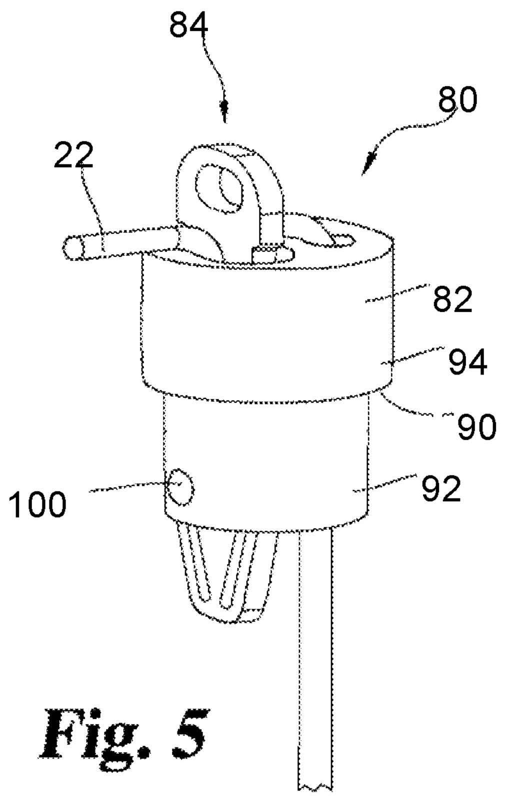
FIG. 5 is a part cross-sectional view of the embodiment of FIG. 3.
Figure 6:
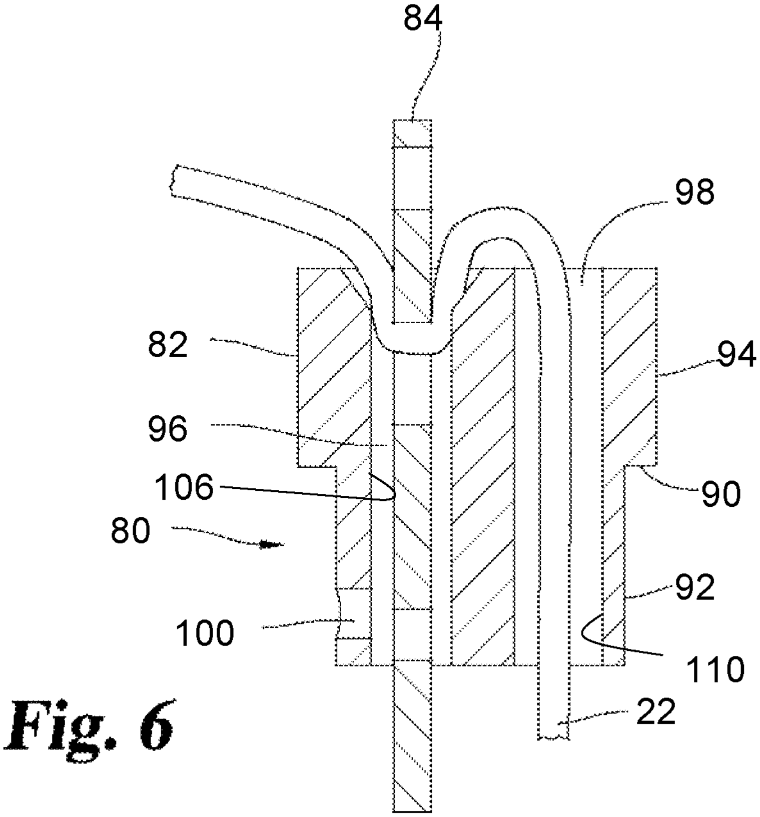
FIG. 6 is a part cross-sectional view of the embodiment of FIG. 4.
Figure 7:
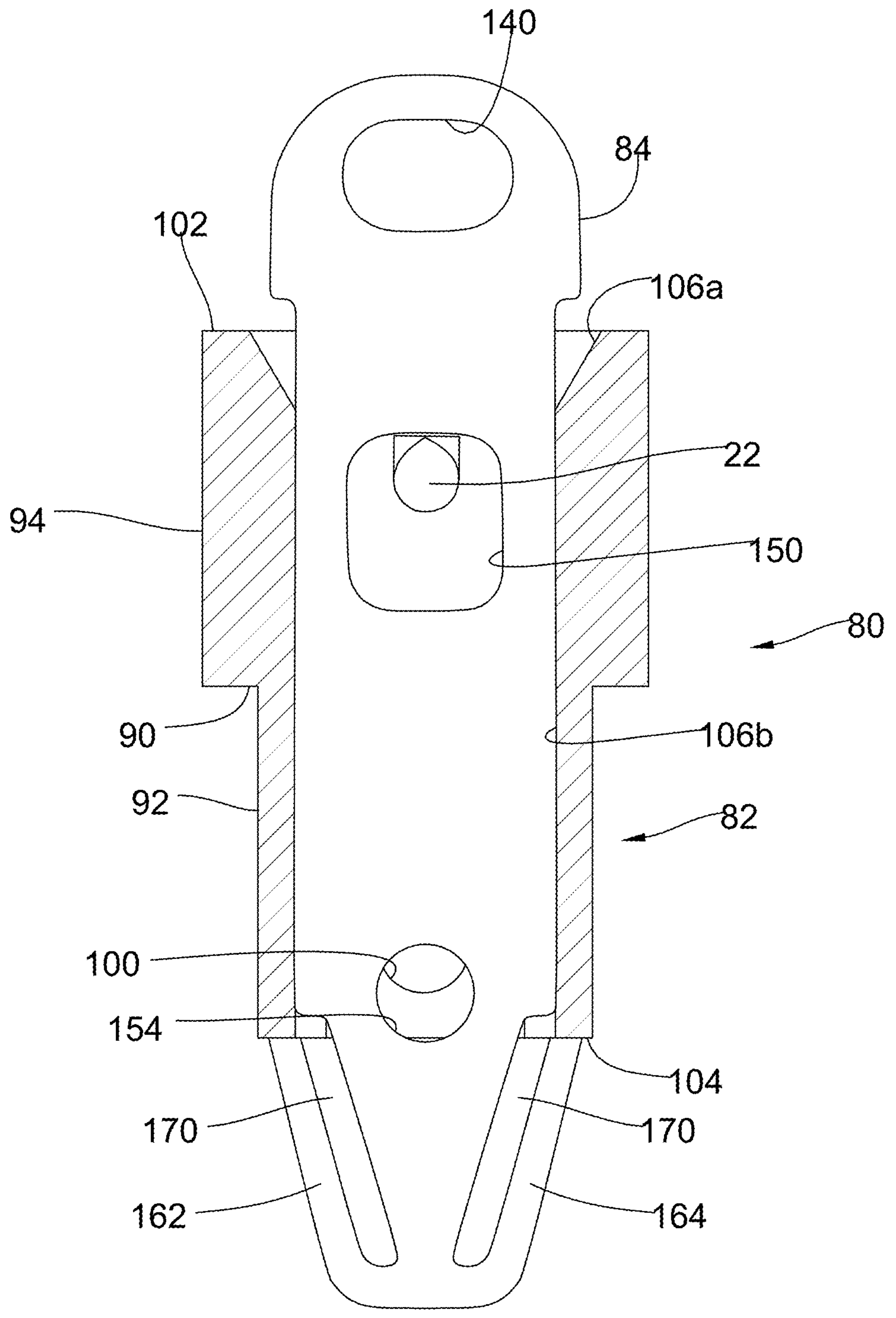
FIG. 7 is a part cross-sectional view of the embodiment of FIG. 6, viewed from the left of FIG. 6.
Figure 8:
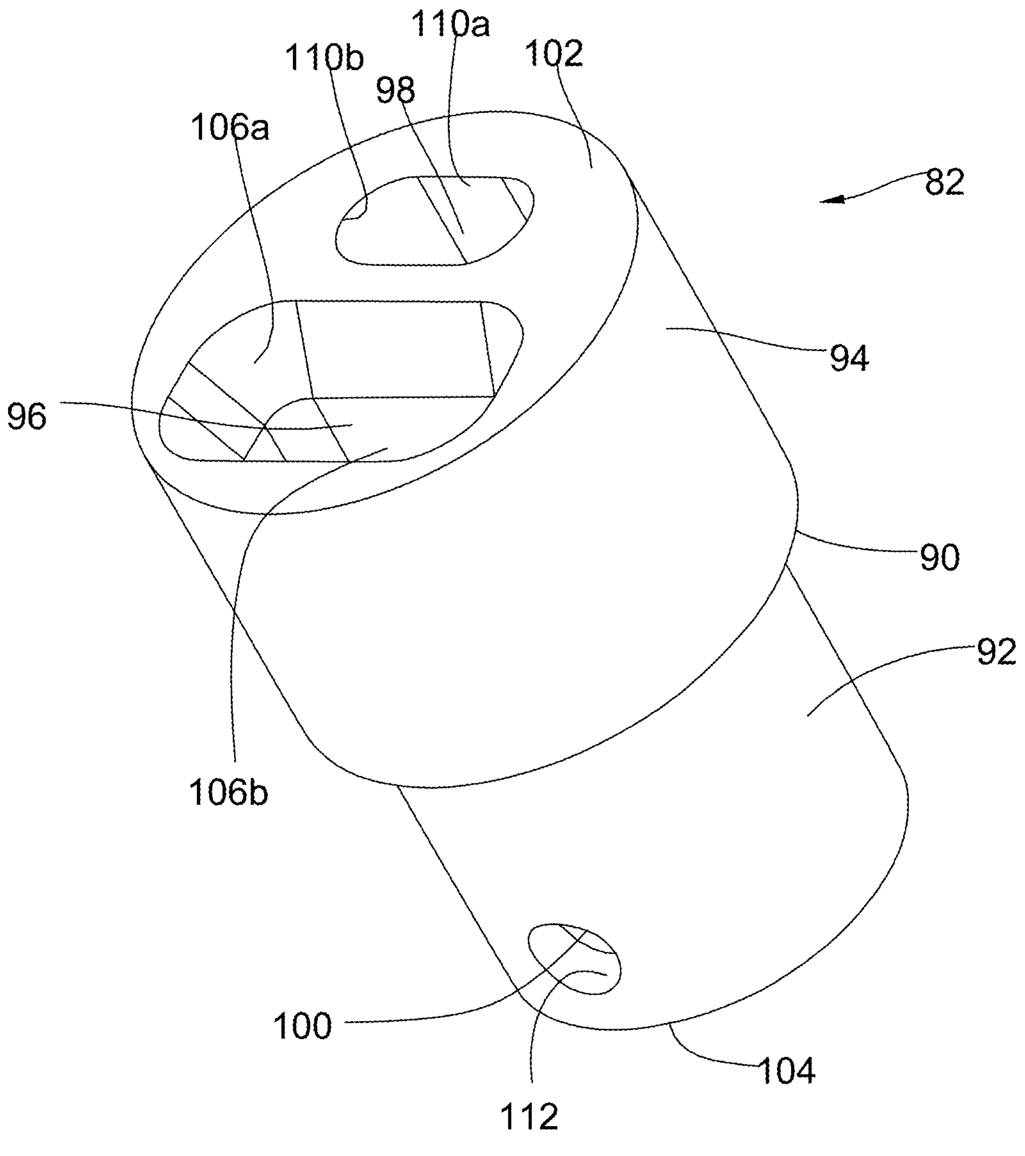
FIG. 8 is a perspective view of an embodiment of a housing of the embodiment of FIG. 3.
Figure 9:
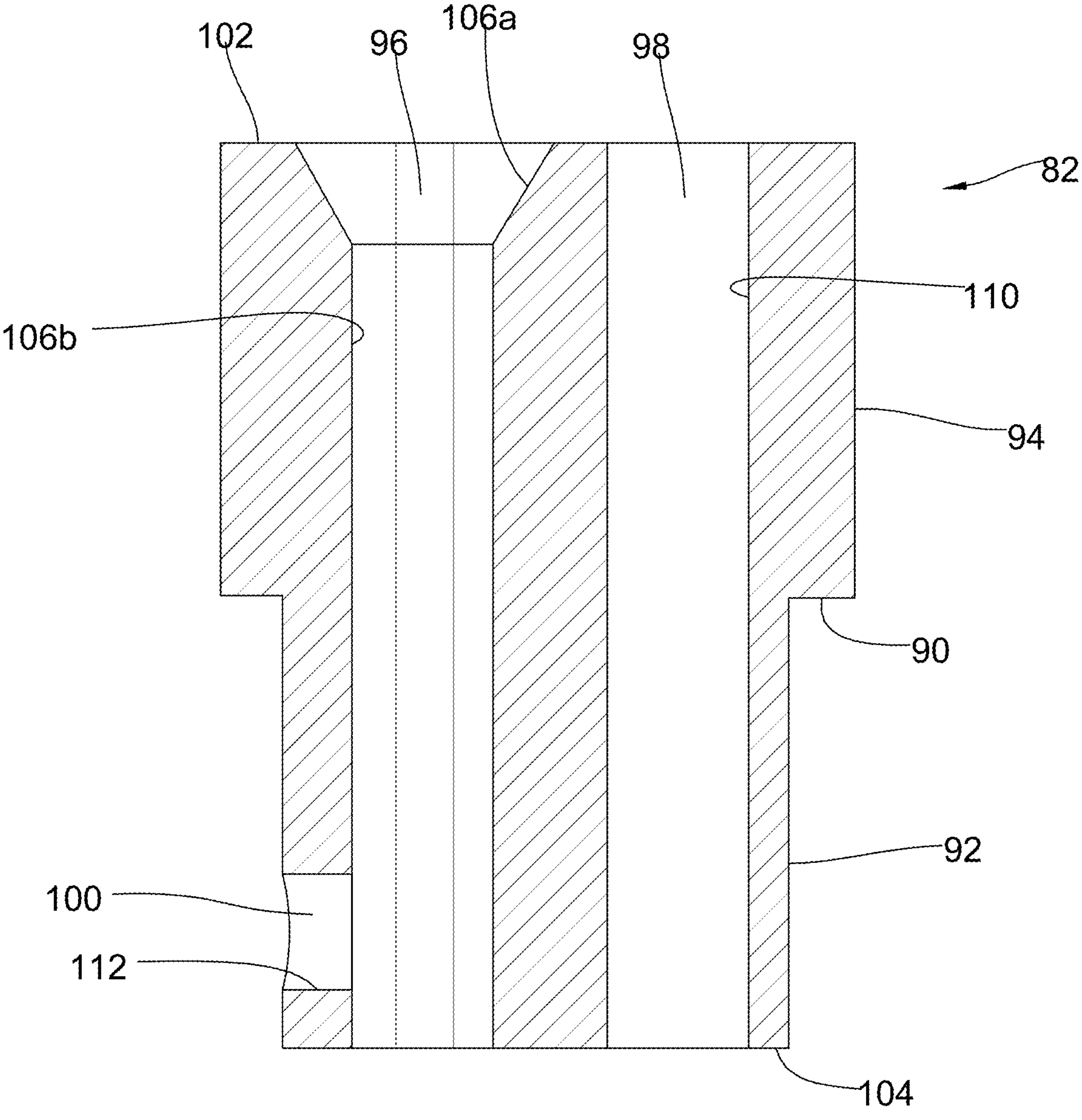
FIG. 9 is a cross-sectional view of the embodiment of FIG. 8.
Figure 10:
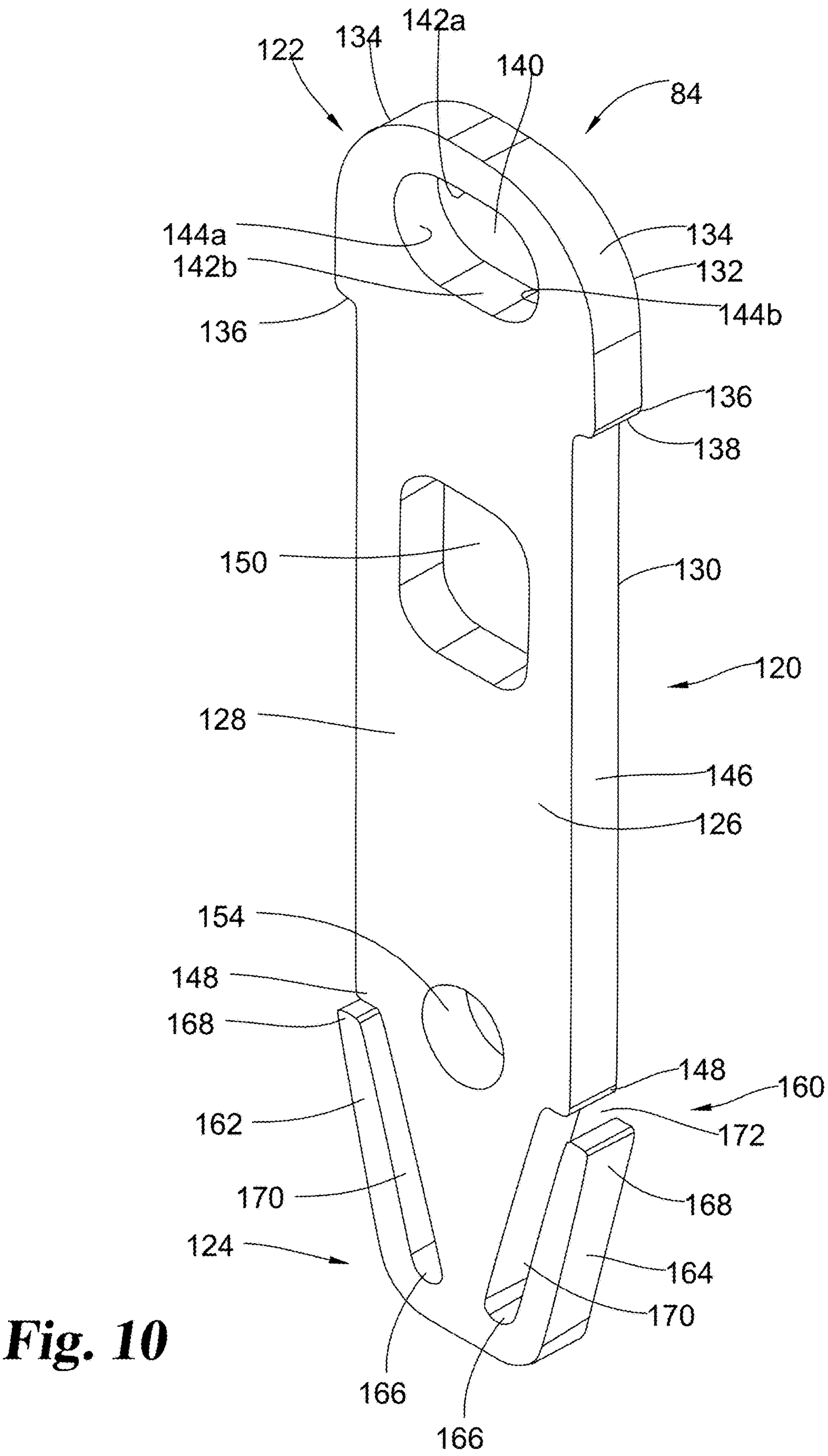
FIG. 10 is a perspective view of an embodiment of a snare of the embodiment of FIG. 3.

To place in the locked state (e.g. FIG. 5-7), snare 84 is pulled or otherwise forced through housing 82. In the illustrated embodiment, snare 84 is force to at least the extent that an edge of middle eyelet 150 (e.g. the edge closest to head portion 132) pulls tensioning suture 22 into through hole 96 with snare 84, and that tabs 162, 164 move past surface 104 of housing 82. By pulling suture 22 into hole 96 (to or through chamfer or conical portion 106*a*), snare 84 and housing 82 force it into a 180-degree bend, S-shaped or similar tortuous configuration. Suture 22 is thus pinched between snare 84 (e.g. edges of eyelet 150 and/or surfaces 128, 130 of body 120) and the inner wall 106 of hole 96. As discussed above, embodiments of hole 96 can include a chamfered or conical portion 106*a*, which allows a smooth transition for suture 22 from the unlocked to the locked state (e.g. allowing the lock to engage with minimal pull force on the snare and/or push force on the housing) and minimizes damage to suture 22 during the locking process. As previously noted, in the illustrated embodiment tabs 162, 164 move past surface 104 of housing 82 to arrive at the locked position. When tabs 162, 164 clear surface 104, the inward force on tabs 162, 164 by inner wall 106 of hole 96 is released, and tabs 162, 164 move outward and open or expand channels 170. As seen in FIGS. 5 and 7, the open tabs 162, 164 extend over surface 104 of housing 82 preventing snare 84 from being retracted into hole 96 of housing 82, and ensuring lock 80 remains locked.

Other embodiments of a locking device are contemplated. For example, suture lock 80' has housing 82 and a snare 84' is similar or identical to snare 84, with the principal difference being at least one middle tab 162'. In this embodiment, tab 162' is cut from or formed in body 120', but is bent out of the plane of body 120'. Tab 162' extends away from body 120' to a distance such that when snare 84' is inserted into hole 96 of housing 82, it is forced inward at least partially by inner wall 106 of hole 96, creating a bias in tab 162'. Similar to the action of snare 84, when snare 84' is moved through hole 96 sufficiently for tab 162' to exit from housing 82 (i.e. when tab 162' clears surface 104 of housing 82), tab 162' springs out a distance sufficient for at least a part of tab 162' to abut surface 104. Like tabs 162, 164, this embodiment with tab 162' provides a latch that is retracted or confined when within housing 82, but springs out after emerging from housing 82 to prevent snare 84' from moving backward into housing 82.

Snare 84' includes a middle eyelet 150' that is rectangular (e.g. square), substantially as described with respect to snare 84. Upper eyelet 140' is circular in this embodiment, and lowermost eyelet 178' is rectangular (e.g. square) and communicates with a slot 170' formed by the bending outward of tab 162'. In this illustrated embodiment, another circular eyelet 154' is between lowermost eyelet 178' and middle eyelet 150'. That additional eyelet 154' may be used in the same way and for the same purpose as lower eyelet 154 of snare 84.

Figure 13:
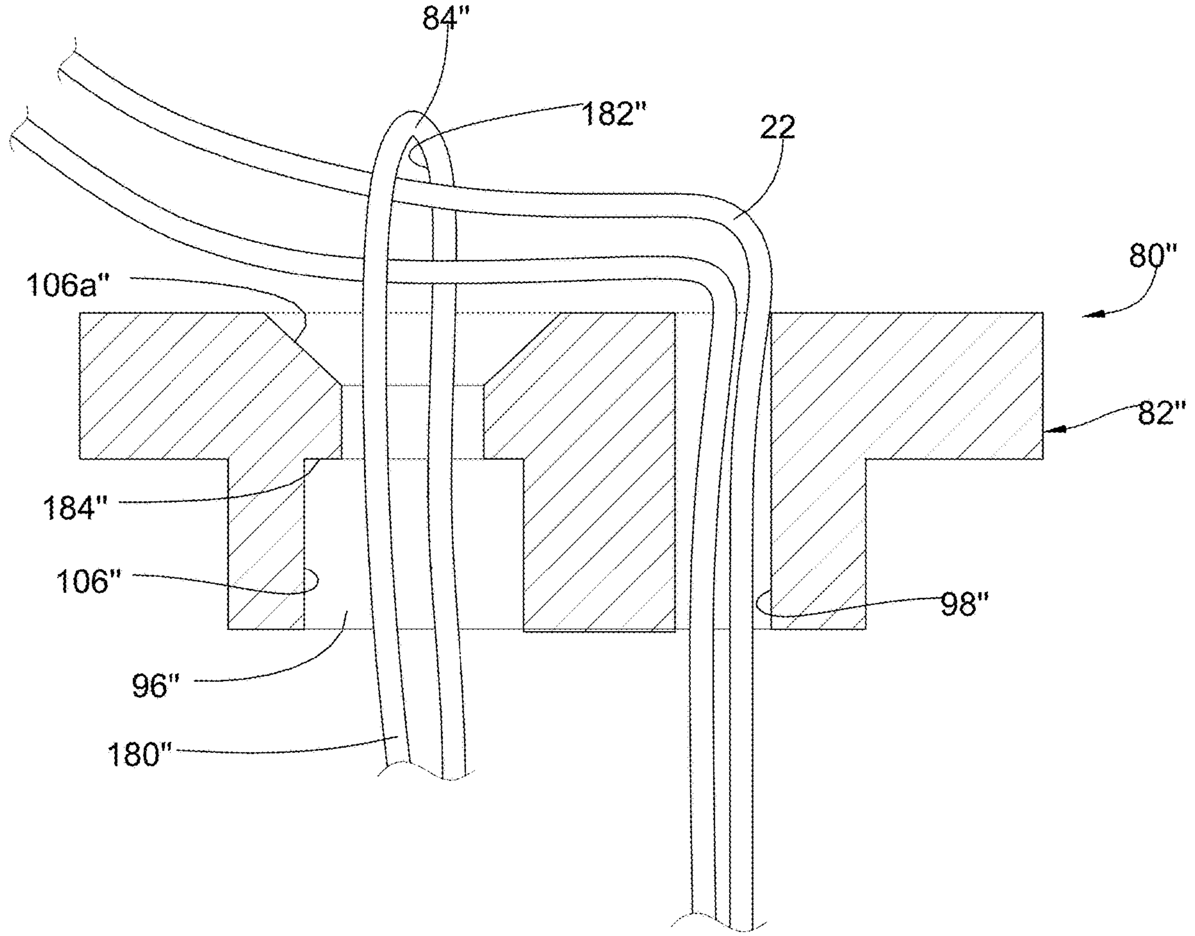
FIG. 13 is a cross-sectional view of an embodiment of a suture lock device with a tensioning suture in an open or unlocked condition, according to the disclosure.

In the embodiment of suture lock 80" shown in FIG. 13, a snare 84" is formed not by a planar body or plate, but by a filament 180". A housing 82" includes a through hole 96" similar to hole 96 described above, with a conical or chamfered portion 106*a*" and a constant dimension (e.g. rectangular, with cross-dimensions each being constant, or cylindrical) portion 106*b*". In this embodiment, the maximum width of the constant dimension portion (e.g. the diameter of a cylindrical portion) is less than twice the width of suture 22. Filament 180" is doubled or otherwise formed into a loop 182". Loop 182" of snare 84" corresponds to eyelet 150 of snare 84, as suture 22 passes through loop 182" and then down through hole 98" of housing 82" (which in this embodiment is identical to hole 98 of housing 82).

Operation of this embodiment is similar to that of lock 80 and snare 84, as suture 22 is tightened by pulling it through loop 182". Pulling filament 180" moves loop 182" into or further through hole 96". Loop 182" pulls a bight in suture 22 into hole 96", wedging the bight (which has double the diameter of suture 22) against the wall of conical/chamfered portion 106*a*" (which may be the top half of hole 96") and/or constant diameter portion 106*b*" of through hole 96". The bight in suture 22 is thus pressed by the walls of hole 96", locking suture 22 in tension in housing 82". In particular embodiments, housing 82" may include an inset or boss 184" within hole 96", which acts as a catch for the bight of suture 22. When the bight is pulled beyond inset 184", suture 22 is not only held by the press of the walls of hole 96", but also by the edge(s) of inset 184" against the sides of the bight in suture 22. In another embodiment, no internal inset 184" is provided, but the bight of suture 22 is pulled through the opening of hole 96" in lower surface 104" of housing 82". The edge(s) of that opening provide friction or pressure against the ability of the bight of suture 22 to pass backward through the opening in surface 104".

Integrated Delivery Assembly

An integrated delivery assembly 200 is also provided, an embodiment of which is shown in FIG. 14. In this embodiment, delivery assembly 200 is designed to operate within an access catheter or sheath, such as a pericardial access sheath 202 that serves as a conduit between a femoral vein access site and the pericardial space through a hole in the right atrial appendage. The illustrated embodiment includes a frame 204 for delivering a belt B (already delivered in FIG. 14), and a pusher catheter 206. In FIG. 14, the heart is not shown for simplicity, but belt B would be delivered around the heart using frame 204. An embodiment of suture lock 80 is shown joined to pusher catheter 206, with tensioning suture 22 being a part of or attached to belt B and extending through lock 80, as described above. An embodiment of tensioning device 20 is within pusher catheter 206 and below lock 80, and is connected to suture 22, as discussed herein.

Sheath 202 may be a part of assembly 200 and introduced or placed at the time that belt B is placed or other aspects of assembly 200 are used, or sheath 202 may be a separate piece placed at a different time or for a different purpose that is then used to pass belt B other aspects of assembly 200. As noted, sheath 202 may be a pericardial access sheath, at least of an inner diameter allowing easy passage of parts of assembly 200 as a unit.

Pusher catheter 206 is a tubular member within sheath 202, and has a lumen 210, which is generally of a constant diameter in the illustrated embodiment but widens at the distal end 212. Distal end 212 includes a ledge or boss 214 that widens lumen 210 from a middle area to end 212, to form a chamber 216 in end 212 generally defined by ledge 214 and side wall 218. Chamber 216 is sized to accommodate a portion of suture lock 80, such as a lower narrowed or inset portion 92 (e.g. FIG. 3) allowing suture lock 80 to nest or seat in chamber 216. Pusher catheter 206 is preferably made of a material with good column strength that resists compression as compressive forces are applied. A preferred material is vinyl. Lock 80 can be fit or squeezed into at least part of chamber 216, for example with a grip by end 212 of catheter 206 on suture lock 80.

The illustrated embodiment of catheter 206 includes a side hole 219 in the wall surrounding chamber 216. Hole 219 is intended to be near or adjacent to side hole 100 of housing 82 of suture lock 80 when suture lock 80 is seated in catheter 206. Catheter 206 is movable at least longitudinally within sheath 202, so as to push suture lock 80 and associated structure out of sheath 202, and/or to adjust the location of suture lock 80 or other structure during placement or operation of assembly 200. Catheter 206 may also be movable laterally and/or in rotation with respect to sheath 202, as may be necessary during use, and/or as may be permitted by other structure (such as frame 204) within sheath 202.

Suture lock 80 includes housing 82 and snare 84 arranged as discussed above in the illustrated embodiment, although it will be understood that other embodiments or parts of a suture lock as disclosed herein may be used. The distal end of the snare 84 is fixed or connected to belt B, e.g. by tying an end of suture 22 that is fixed to one end of belt B to snare 84. In particular embodiments, the end of suture 22 from one end of belt B may be looped around head portion 132 of snare 84 through eyelet 140 and tied. Suture 22 passes through belt B. Suture 22 extends from the other end of belt B and passes through a second, larger eyelet (e.g. middle eyelet 150) in snare 84, into and through hole 98 through housing 82, and emerges into chamber 216 or another part of lumen 210 of pusher catheter 206.

Within lumen 210 and proximal of suture lock 80 is tensioning device 20, which may be or include any of the structures or embodiments discussed above. Tensioning device 20, as noted previously, is used to control the position of the free end of tensioning suture 22.

Assembly 200 includes a pair of trigger wires 220, 222 in this embodiment that control the function of suture lock 80. Wires 220, 222 are of nitinol or stainless steel in particular embodiments. A safety and anchor trigger wire 220, shown extending through lumen 210 on the left side of pusher catheter 206, prevents snare 84 from pulling into housing 82 and restricts motion of tensioning suture 22 prematurely. It also serves to anchor the lock housing 82 to pusher catheter 206. Wire 220 passes through housing 82 of suture lock 80, going into the lower end of hole 96 (in which snare 84 resides) and exiting housing 82 via side hole 100. Wire 220 then passes through side hole 219 of pusher catheter 206, effectively pinning housing 82 of suture lock 80 to pusher catheter 206. Wire 220 may extend partially or fully around the outside of catheter 206 in particular embodiments (e.g. FIG. 16), and may be composed of a sturdy shape-memory material such as nitinol. Because wire 220 enters through hole 96 that is used for snare 84, it blocks or limits snare 84 from moving proximally through hole 96 prior to removal of wire 220, preventing locking of lock 80.

Figure 15:
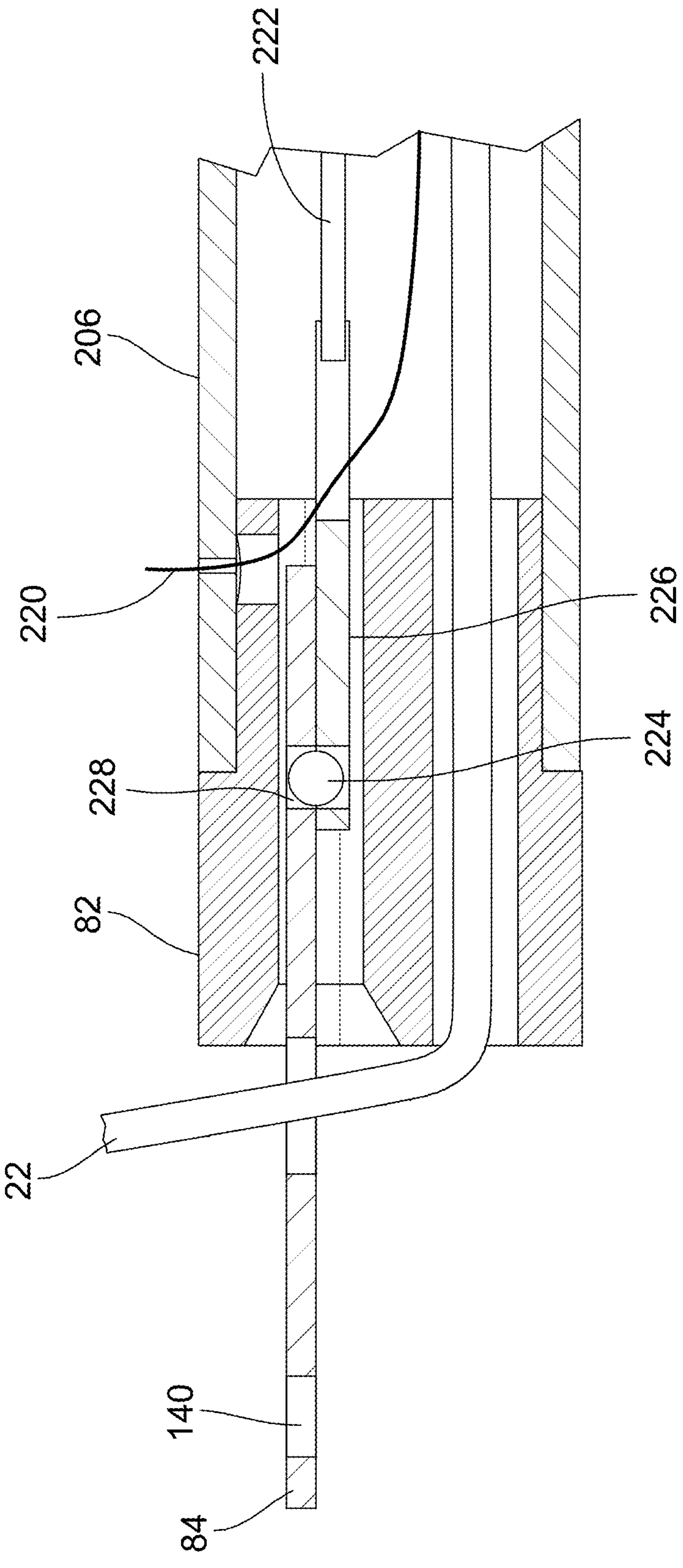
FIGS. 15 and 16 are part cross-sectional views of the embodiment of FIG. 3 showing triggering and safety/anchor wire structure.
Figure 16:
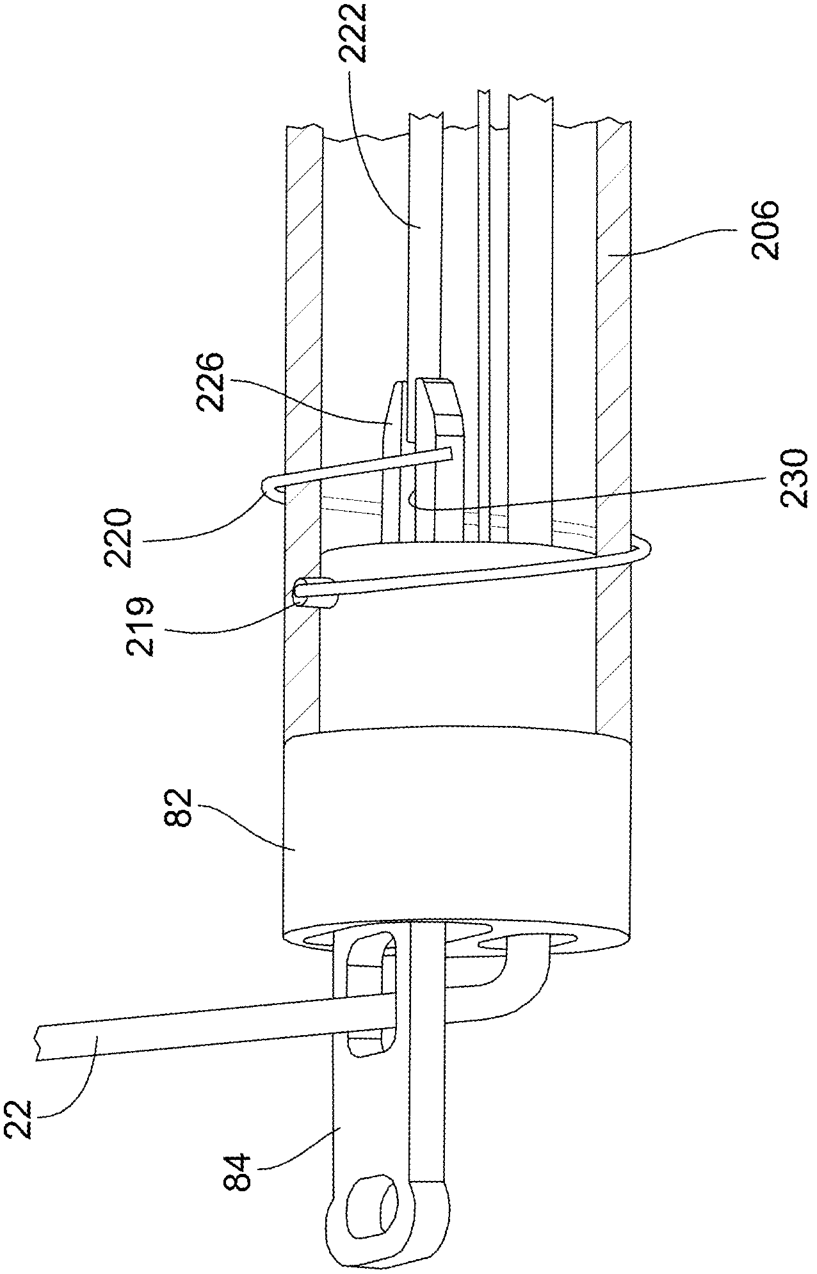

Locking trigger wire 222 is as described above in the context of suture lock 80. In the illustrated embodiment, wire 222 is just to the right of safety and anchor trigger wire 220. Wire 222 has a small ball 224 welded or otherwise fixed to its distal end, and ball 224 nests in lower eyelet 154 in snare 84. In the example of FIGS. 15-16, wire 222 includes a support or plate 226 having a hole 228 in which ball 224 is fixed, and a slot 230 through which safety wire 220 runs so as to block or limit distal travel of support 226 and snare 84. Ball 224 is fixed in hole 228 so that at least a part (for example half or more) extends from hole 228 into eyelet 154 when suture lock 80 is assembled and not locked. Ball 224 is preferably radiopaque or otherwise visible on fluoroscopy or other imaging systems, so that the user can confirm during the procedure positioning and/or engagement of suture lock 80.

After safety/anchor trigger wire 220 is pulled out, removing it from holes 219 and 100 and out of housing 82 of suture lock 80 so that it does not block or limit snare 84 and/or support 226, wire 222 is moved with respect to lock 80, as by pulling wire 222 or by holding wire 22 steady as lock 80 is pushed forward by catheter 206. Ball 224 nested in snare 84 pulls snare 84 (with support 226, if present) through hole 96 and deeper into housing 82. In a particular example, wire 222 may be maneuvered (as noted above) partially to pin suture 22 with housing 82 (e.g. against surface(s) 106*a*) without fully locking. A proximal portion of suture 22 can be loosened (from the left as seen in FIGS. 3-6) to provide some slack. Wire 222 is then pulled further, drawing such slack in suture 22 into housing 82 (e.g. into lumen 96) to fully lock the suture. Providing such slack allows full locking to occur without overtensioning suture 22, reducing or eliminating risk of fracturing suture 22. As discussed above, snare 84 pulls tensioning suture 22 with it into housing 82, locking suture 22 in suture lock 80. Tabs 162, 164 (e.g. FIGS. 5, 7) pop out once they clear the bottom surface 104 of housing 82, preventing snare 84 from returning distally through hole 96 and from releasing suture 22.

As snare 84 is pulled down, ball 224 becomes exposed below housing 84 and exits eyelet 154 of snare 84. Ball 224 (and support 226 if present) can eventually clear housing 82. With ball 224 free from snare 84, and wire 220 previously having been removed, suture lock 80 and locked suture 22 is releasable from catheter 206. With belt B placed around the heart and suture 22 tightened as appropriate for therapy, assembly 200 can be removed from the treatment site. Fluoroscopy or other imaging methods may be used during the procedure to confirm placement and engagement of belt B and/or suture lock 80.

In particular methods of using assembly 200, a belt B is initially loaded onto delivery frame 204. Frame 204 with belt B starts out loaded in delivery sheath 202 at a location distal to pusher catheter 206 and suture lock 80 seated in the distal end of pusher catheter 206. Frame 204 and belt B is exposed from delivery sheath 202, as by moving frame 204 out of the distal end of delivery sheath 202, or by pulling sheath 202 back with respect to frame 204. Once exposed, frame 204 expands and the user encircles the heart with frame 204 and annuloplasty belt B.

Belt B is tensioned while still loaded on frame 204 in particular embodiments. Tensioning device 20 is slid proximally (down as seen in FIG. 14) within pusher catheter 206 while tensioning suture 22 is locked to or otherwise held by tensioning device 20, as described above. For example, tensioning device 20 pulls suture 22 through hole 98 of housing 82 and eyelet 150 of snare 84 of suture lock 80. Tension is applied to configure belt B (to which suture 22 is attached) as the user desires, e.g. to place compression around and/or on a particular part of the heart without damage to vessels or other cardiac structures. Once slack in belt B is taken up, delivery frame 204 is withdrawn from inside belt B and into sheath 202 alongside pusher catheter 206. Tension on suture 22, and thereby belt B, can be adjusted by further positioning of tensioning device 20. For example, sliding tensioning device 20 distally with respect to catheter 206 and sheath 202 (up as seen in FIG. 14) will release tension and loosen belt B, and sliding tensioner proximally with respect to catheter 206 and sheath 202 will add tension to tighten belt B.

Once proper tension for the desired therapy is established in suture 22, safety/anchor trigger wire 220 is pulled through side hole 219 of catheter 206 and side hole 100 of housing 82 so that the distal end of wire 22 is within lumen 210 of catheter 206. Suture lock 80 is thus enabled to be set, as wire 220 no longer blocks movement of snare 84 further into housing 82. Lock trigger wire 222 is pulled, pulling snare 84 proximally further into housing 82. Snare 84 (and particularly the edge(s) of eyelet 150 in the illustrated embodiment) pulls tensioning suture 22 to a locked position, e.g. into hole 96 of housing 82 to place suture 22 in a tortuous configuration and/or wedge suture 22 with respect to snare 84 and the wall(s) 106 of hole 96 of housing 82. Tabs 162, 164 latch snare 84 in place, and ball 224 at the distal end of wire 222 escapes from snare 84, as noted above. As an alternative to pulling wire 222 to move snare 84 through housing 82, it can be moved with respect to catheter 206 by keeping wire 222 held in its position and advancing pusher catheter 206.

With belt B placed, tension applied to it via suture 22, and that tension locked via suture lock 80, tensioning device 20 is released from suture 22. In the illustrated embodiment, release wire and/or loop 32, 33' (discussed above) is pulled from tensioning device 20. Suture 22 is thereby released from tensioning device 20. Delivery sheath 202, with pusher catheter 206, frame 204 and/or tensioning device 20 within it, is withdrawn from the treatment site, leaving belt B, tensioning suture 22 and suture lock 80 within the body. It will be understood that parts of assembly 200 may be earlier withdrawn after their use(s) have been completed, rather than waiting for completion of all steps for withdrawal. For example, once frame 204 is withdrawn from belt B as noted above, it may be removed from delivery sheath 202 and the body at that time, rather than following the release of suture 22 from tensioning device 20.

Assembly 200 also provides a method for withdrawal of belt B from the patient prior to locking and after belt B has been placed around the heart, e.g. if there is an error, emergency or other indication that belt B should be removed. In one example, once the decision to remove belt B has been taken, the tensioning suture 22 is released from tensioning device 20, and tensioning device 20 may be withdrawn along or out of pusher catheter 206 and/or delivery sheath 202. Suture lock 80 remains anchored to pusher catheter 206 by wire 222, and ball 224 remains engaged to snare 84 of suture lock 80. That is, neither trigger wire 220, 222 is pulled from suture lock 80. Delivery sheath 202 is then withdrawn with pusher catheter 206 and suture lock 80 connected to catheter 206, causing tensioning suture 22 to unthread through hole 98 of housing 82 and eyelet 150 of snare 84 of suture lock 80. The connection between suture 22 and upper eyelet 140 of snare 84 is maintained, so that withdrawing suture lock 80 (with ball 224 and wire 222 keeping snare 84 linked to housing 82) pulls belt B around the heart and out of the body with assembly 200.

It will be understood that the features disclosed above may be connected, directly or by intervening structure, to an operating handle or system located outside of the patient. Thus, wires 32 and/or 34 of tensioning device 20, and in some embodiments tube 30 of tensioning device 20, may extend through pusher catheter 206 and/or delivery sheath 202 to a handle directly or via other structures, so that wires 32, 34 and/or tensioning device 20 as a whole can be retracted or extended as necessary by an operator. Similarly, wires 220, 222 may extend through pusher catheter 206 and/or delivery sheath 202 (directly or via other structures) to the same or a different handle, so that wires 220, 222 can be retracted as appropriate by an operator. Such a handle, or a separate item, may be used to place belt B and withdraw frame 204.

While the disclosure has been illustrated and described in detail in the drawings and foregoing description, the same is to be considered as illustrative and not restrictive in character, it being understood that only selected embodiments have been shown and described and that all equivalents, changes, and modifications that come within the spirit of the disclosures as defined herein or by the following claims are desired to be protected. It will be understood that features described particularly with respect to one or more specific structures or embodiments may be incorporated into or otherwise used with other structures or embodiments as disclosed herein.

The following numbered clauses set out specific embodiments that may be useful in understanding the present invention:

1. A tensioning device for placing tension on a tensioning suture connected to an annuloplasty belt, comprising:

a tubular outer member having a lumen and a distal opening of the lumen, the tubular outer member having an end surface around the distal opening;

a first wire having an end portion around which the tensioning suture is passed, the first wire being within the lumen so that the end portion extends beyond the distal opening;

a second wire having an end loop between two leg portions, the second wire being within the lumen so that at least part of the leg portions are within the lumen and the end loop is outside of the tubular outer member beyond the distal opening;

wherein in an extended configuration the end portion of the first wire extends beyond the end loop of the second wire, and wherein the tensioning suture passes one of under and through the end loop of the second wire, so that pulling the second wire engages the tensioning suture and pulls the tensioning suture, and the first wire anchors the tensioning suture with respect to the second wire during the pulling.

2. The tensioning device of clause 1, wherein the lumen has an inner diameter, and wherein the end loop has a maximum lateral dimension that is larger than the inner diameter of the lumen.

3. The tensioning device of any of clauses 1 or 2, wherein the first wire has a straight end portion and passes through the end loop of the second wire, and wherein in the extended configuration the tensioning suture passes around the end portion of the first wire between the end loop of the second wire and the end surface of the tubular outer member.

4. The tensioning device of clause 3, wherein the first wire is retractable with respect to the second wire, and wherein in a retracted configuration the end portion of the first wire does not extend through the end loop of the second wire, but is below the end loop so that the tensioning suture can be passed out from between the end loop and the end surface of the tubular outer member.

5. The tensioning device of any of clauses 1-4, wherein the end portion of the first wire includes a looped end portion joining at least one leg, and wherein in the extended configuration at least part of the end loop of the second wire is between the end surface of the tubular outer member and at least part of the looped end portion of the first wire, and wherein the tensioning suture passes through the end loop of the second wire and around the at least one leg of the first wire below the looped end portion of the first wire.

6. The tensioning device of clause 5, wherein the first wire is retractable with respect to the second wire, and wherein in a retracted configuration the looped end portion of the first wire is retracted relative to the second wire so that the tensioning suture does not pass around the at least one leg or the looped end portion of the first wire.

7. The tensioning device of any of clauses 1-6, wherein the lumen has a diameter the same as or slightly larger than the sum of the diameters of the portions of the first wire and second wire within the lumen, so that the tensioning suture is not pulled into the lumen.

8. A suture lock for holding a tensioning suture in tension, comprising:

a housing having first and second through holes extending between a distal surface and a proximal surface, the first and second through holes being laterally separated, the housing having a side hole through a side surface and adjacent the proximal surface, the side hole communicating with the first through hole;

a snare within the first through hole and adapted to move longitudinally through the first through hole, the snare having an opening;

an anchor wire passing through a proximal portion of the first through hole and through the side hole;

wherein the suture lock has an open configuration in which the opening of the snare is at least partially out of the first through hole and the tensioning suture passes through the opening of the suture and the second through hole of the housing and can be freely translated with respect to the snare and the second through hole of the housing, and a locked configuration in which the opening of the snare is within the first through hole and the tensioning suture is held against translation by the snare in a tortuous configuration.

9. The suture lock of clause 8, wherein the snare is a planar body and the opening is a middle eyelet allowing passage of the tensioning suture, the snare including an upper eyelet for attachment to a portion of the tensioning suture and a lower eyelet for accommodating a trigger wire.

10. The suture lock of clause 9, wherein the trigger wire includes a ball fixed to an end of the trigger wire, the ball fitted into the lower eyelet of the snare, whereby pulling the trigger wire and ball pulls the snare through the first through hole of the housing.

11. The suture lock of any of clauses 8-10, wherein the snare includes at least one tab, the at least one tab joined to and extending from a proximal portion of the snare, so that in the open configuration the at least one tab is bent toward the body of the snare by and remains biased against a wall of the first through hole of the housing, and in the locked configuration the at least one tab is beyond the proximal surface of the housing and pivoted outward from the snare so that the at least one tab prevents retraction of the snare into the first through hole.

12. The suture lock of clause 11, wherein the snare includes two lateral tabs, both tabs are bent toward the body of the snare in the plane of the snare in the open configuration.

13. The suture lock of clause 11, wherein the at least one tab extends out of the plane of the snare, so that in the open configuration the at least one tab is bent toward the plane of the snare and in the locked configuration the at least one tab pivots away from the plane of the snare.

14. The suture lock of any of clauses 8-13, wherein the snare includes filament and the opening is a loop in the filament.

15. The suture lock of any of clauses 8-13, wherein the housing includes an inset in the first through hole, wherein in the locked configuration the tensioning suture engages the inset.

16. An integrated delivery system for an annuloplasty belt, comprising:

a delivery sheath;

a pusher catheter within the delivery sheath having an internal lumen;

a suture lock connected to a distal end of the pusher catheter;

an annuloplasty belt having a tensioning suture, the annuloplasty belt being beside the pusher catheter within the delivery sheath; and a tensioning device for applying tension to the tensioning suture within lumen of the pusher catheter and proximal of the suture lock, wherein a first end of the tensioning suture is fixed to a portion of the suture lock, a middle portion of the tensioning suture passes through the suture lock and a second end of the tensioning suture is connected to the tensioning device.

17. The system of clause 16, wherein the lumen of the pusher catheter includes a proximal portion with a first inner diameter and an end chamber having a second inner diameter larger than the first inner diameter, and wherein the suture lock is fitted within the end chamber of the pusher catheter.

18. The system of any of clauses 16 or 17, wherein the suture lock is the suture lock of claim 8.

19. The system of any of clauses 16-18, wherein the suture lock includes a proximal side hole and the pusher catheter includes a side hole in a distal end, wherein the side hole of the suture lock and the side hole of the pusher catheter at least overlap, and further comprising a safety/anchor wire that extends through the side hole of the suture lock and the side hole of the pusher catheter to hold the suture lock and pusher catheter together.

20. The system of clause 19, further comprising a trigger wire connected to the suture lock by which to lock the tensioning suture within the suture lock, the trigger wire and the safety/anchor wire extending through the lumen of the pusher catheter.

What is claimed:

1. An integrated delivery system for an annuloplasty belt comprising:

a delivery sheath;

a pusher catheter within the delivery sheath having an internal lumen;

a suture lock connected to a distal end of the pusher catheter, the suture lock comprising:

a housing having first and second through holes extending between a distal surface and a proximal surface, the first and second through holes being laterally separated, the housing having a side hole through a side surface and adjacent the proximal surface, the side hole communicating with the first through hole;

a snare within the first through hole and adapted to move longitudinally through the first through hole, the snare having an opening; and an anchor wire passing through a proximal portion of the first through hole and through the side hole;

wherein the suture lock has an open configuration in which the opening of the snare is at least partially out of the first through hole and the tensioning suture passes through the opening of the snare and the second through hole of the housing and can be freely translated with respect to the snare and the second through hole of the housing, and a locked configuration in which the opening of the snare is within the first through hole and the tensioning suture is held against translation by the snare in a tortuous configuration;

an annuloplasty belt having a tensioning suture, the annuloplasty belt being beside the pusher catheter within the delivery sheath; and a tensioning device within the lumen of the pusher catheter and proximal of the suture lock, the tensioning device for applying tension to the tensioning suture, wherein a first end of the tensioning suture is fixed to a portion of the suture lock, a middle portion of the tensioning suture passes through the suture lock and a second end of the tensioning suture is connected to the tensioning device.

2. The system of claim 1, wherein the snare is a planar body and the opening is a middle eyelet allowing passage of the tensioning suture, the snare including an upper eyelet for attachment to a portion of the tensioning suture and a lower eyelet for accommodating a trigger wire.

3. The system of claim 2, wherein the trigger wire includes a ball fixed to an end of the trigger wire, the ball fitted into the lower eyelet of the snare, whereby pulling the trigger wire and ball pulls the snare through the first through hole of the housing.

4. The system of claim 2, wherein the snare includes at least one tab, the at least one tab joined to and extending from a proximal portion of the snare, so that in the open configuration the at least one tab is bent toward the body of the snare by and remains biased against a wall of the first through hole of the housing, and in the locked configuration the at least one tab is beyond the proximal surface of the housing and pivoted outward from the snare so that the at least one tab prevents retraction of the snare into the first through hole.

5. The system of claim 4, wherein the at least one tab comprises two lateral tabs, both of the tabs bent toward the body of the snare in a plane of the snare in the open configuration.

6. The system of claim 4, wherein the at least one tab extends out of a plane of the snare, so that in the open configuration the at least one tab is bent toward the plane of the snare and in the locked configuration the at least one tab pivots away from the plane of the snare.

7. The system of claim 1, wherein the snare includes a filament and the opening is a loop in the filament.

8. The system of claim 1, wherein the housing includes an inset in the first through hole, wherein in the locked configuration the tensioning suture engages the inset.

9. An integrated delivery system for an annuloplasty belt, comprising:

a delivery sheath;

a pusher catheter within the delivery sheath having an internal lumen;

a suture lock connected to a distal end of the pusher catheter, wherein the suture lock includes a proximal side hole and the pusher catheter includes a side hole in a distal end, wherein the side hole of the suture lock and the side hole of the pusher catheter are adjacent to one another, and further comprising a safety/anchor wire that extends through the side hole of the suture lock and the side hole of the pusher catheter to hold the suture lock and pusher catheter together;

an annuloplasty belt having a tensioning suture, the annuloplasty belt being beside the pusher catheter within the delivery sheath; and a tensioning device within the lumen of the pusher catheter and proximal of the suture lock, the tensioning device for applying tension to the tensioning suture, wherein a first end of the tensioning suture is fixed to a portion of the suture lock, a middle portion of the tensioning suture passes through the suture lock and a second end of the tensioning suture is connected to the tensioning device.

10. The system of claim 9, further comprising a trigger wire connected to the suture lock by which to lock the tensioning suture within the suture lock, the trigger wire and the safety/anchor wire extending through the lumen of the pusher catheter.

* * * * *